US010808057B2

(12) United States Patent
Choi et al.

(10) Patent No.: US 10,808,057 B2
(45) Date of Patent: Oct. 20, 2020

(54) MODIFIED CONJUGATED DIENE-BASED POLYMER AND METHOD OF PREPARING THE SAME

(71) Applicant: LG Chem, Ltd., Seoul (KR)

(72) Inventors: Seung Ho Choi, Daejeon (KR); Dae June Joe, Daejeon (KR); Won Taeck Lim, Daejeon (KR); Won Mun Choi, Daejeon (KR)

(73) Assignee: LG Chem, Ltd. (KR)

( * ) Notice: Subject to any disclaimer, the term of this patent is extended or adjusted under 35 U.S.C. 154(b) by 148 days.

(21) Appl. No.: 16/084,044

(22) PCT Filed: Oct. 30, 2017

(86) PCT No.: PCT/KR2017/012066
§ 371 (c)(1),
(2) Date: Sep. 11, 2018

(87) PCT Pub. No.: WO2018/084512
PCT Pub. Date: May 11, 2018

(65) Prior Publication Data
US 2020/0123287 A1 Apr. 23, 2020

(30) Foreign Application Priority Data

Nov. 1, 2016 (KR) .......................... 10-2016-0144741
Oct. 26, 2017 (KR) .......................... 10-2017-0139991

(51) Int. Cl.
C08F 136/06 (2006.01)
C07C 227/14 (2006.01)
C07C 227/18 (2006.01)
C07C 249/02 (2006.01)
C07C 251/08 (2006.01)
C08C 19/22 (2006.01)

(52) U.S. Cl.
CPC .......... C08F 136/06 (2013.01); C07C 227/14 (2013.01); C07C 227/18 (2013.01); C07C 249/02 (2013.01); C07C 251/08 (2013.01); C08C 19/22 (2013.01)

(58) Field of Classification Search
CPC .......... C07F 7/10; C08C 19/22; C08F 136/06; C08F 2/38; C08F 2810/40; C08F 8/30; C07C 227/14; C07C 227/18; C07C 249/02; C07C 251/08
See application file for complete search history.

(56) References Cited

U.S. PATENT DOCUMENTS 5,064,907 A    11/1991  Bronstert et al.
5,334,665 A *   8/1994  Lawson .................. C08C 19/44
                                                    525/289
7,968,652 B2 *  6/2011  Kurazumi ................. B60C 1/00
                                                    525/351

2004/0176514 A1   9/2004  Kubo et al.
2006/0135790 A1*  6/2006  Hyett ..................... C07C 253/30
                                                      548/530
2009/0203826 A1*  8/2009  Rachita ..................... B60C 1/00
                                                      524/445
2009/0229729 A1*  9/2009  Woloszynek ........... C07F 5/025
                                                      152/548
2009/0236974 A1   9/2009  Tamaru et al.
2009/0292043 A1  11/2009  Kurazumi et al.
2010/0075948 A1   3/2010  Ding et al.
2010/0280011 A1  11/2010  deLong et al.
2012/0184677 A1   7/2012  Luo
2013/0319589 A1  12/2013  Sato
2014/0135356 A1   5/2014  Sun
2016/0264698 A1   9/2016  Qin et al.
2017/0204205 A1*  7/2017  Choi ........................ C08K 3/36

FOREIGN PATENT DOCUMENTS

| CN | 1756735 A      | 4/2006  |
| CN | 104204000 A    | 12/2014 |
| JP | S60130603 A    | 7/1985  |
| JP | H01221404 A    | 9/1989  |
| JP | 2009221203 A   | 10/2009 |
| JP | 2012502940 A   | 2/2012  |
| JP | 2012525386 A   | 10/2012 |
| JP | 2013093587 A   | 5/2013  |
| JP | 2013249421 A   | 12/2013 |
| JP | 2014177520 A   | 9/2014  |
| KR | 20040014574 A  | 2/2004  |
| KR | 20160065015 A  | 6/2016  |
| KR | 20160076248 A  | 6/2016  |
| WO | 0134659 A1     | 5/2001  |
| WO | 2006112450 A1  | 10/2006 |
| WO | 2010127330 A1  | 11/2010 |

(Continued)

OTHER PUBLICATIONS

Extended European Search Report including the Written Opinion for Application No. EP 17867965.0 dated Apr. 11, 2019.
Search report from International Application No. PCT/KR2017/012066, dated Feb. 5, 2018.
Strohmeier, M., et al., "Asymmetric Conjugate Addition of Glycine Derivatives Under Copper Catalysis." Angew. Chem. Int. Ed., vol. 50, (Received: Jul. 26, 2011; Revised: Sep. 28, 2011; Published online: Oct. 26, 2011), pp. 12335-12338.
Duhamel et al., Enantioselective Alkylation o Enolate Dervied from Glycine Influence of the Imine Moiety, Tetrahedron Letters, vol. 25, No. 22, 1984, pp. 2355-2358.
Hyett et al., A Method for the Preparation of Functionalized Unnatural a-H-a-mino Acid Derivatives, Tetrahedron Letters, 47, 2006, pp. 7771-7774.
Ikota et al., Stereochemical Studies LIX Asymmetric Transamination from (S)-a-Amino Acids. Synthesis of Optically Active Amines by Chemical Transamination of (S)-a-Amino Acid Esters to Ketones, Chem. Pharm. Bull., 31 (3), 1983, pp. 887-894.

(Continued)

Primary Examiner — Robert C Boyle
(74) Attorney, Agent, or Firm — Lerner, David, Littenberg, Krumholz & Mentlik, LLP

(57) ABSTRACT

The present invention relates to a modifier represented by Formula 1, a method of preparing the same, a modified conjugated diene-based polymer having a high modification ratio which includes a modifier-derived functional group, and a method of preparing the polymer.

9 Claims, No Drawings

(56) References Cited

FOREIGN PATENT DOCUMENTS

WO    2011098398 A1    8/2011
WO    2015050947 A1    4/2015

OTHER PUBLICATIONS

O'Donnell, et al., The Preparation of Optically Active a-Amino Acids from the Benzophenone Imines of Glycine Derivatives, 1951-2001: Fifty Years of Chemists Helping Chemists, Aldrichimica ACTA, vol. 34, No. 1, 2001, pp. 3-15.
Search Report from Chinese Office Action for Application 201780018519.4 dated Nov. 1, 2019.
Yamada et al., Asymmetric Transamination from Amino Acids (II) Asymmetric Synthesis of Amines by Chemical Transamination of Optically Active Amino Acid to Ketones, Tetrahedron Letters No. 13, Pergamon Press, Great Britain, 1976, pp. 1001-1004.

* cited by examiner

MODIFIED CONJUGATED DIENE-BASED POLYMER AND METHOD OF PREPARING THE SAME

CROSS-REFERENCE TO RELATED APPLICATIONS

The present application is a national phase entry under 35 U.S.C. § 371 of International Application No. PCT/KR2017/012066 filed Oct. 30, 2017, which claims priority from Korean Patent Application Nos. 10-2016-0144741, filed on Nov. 1, 2016, and 10-2017-0139991, filed on Oct. 26, 2017, the disclosures of which are incorporated herein by reference.

TECHNICAL FIELD

The present invention relates to a modifier useful for polymer modification, a modified conjugated diene-based polymer including a modifier-derived functional group, and a method of preparing the polymer.

BACKGROUND ART

In line with the recent demand for fuel-efficient cars, a conjugated diene-based polymer having adjustment stability represented by wet skid resistance as well as low rolling resistance and excellent abrasion resistance and tensile properties is required as a rubber material for a tire.

In order to reduce the rolling resistance of a tire, there is a method of reducing a hysteresis loss of a vulcanized rubber, and rebound resilience at 50° C. to 80° C., tan δ, or Goodrich heat generation is used as an evaluation index of the vulcanized rubber. That is, it is desirable to use a rubber material having high rebound resilience at the above temperature or low tan δ or Goodrich heat generation.

A natural rubber, a polyisoprene rubber, or a polybutadiene rubber is known as a rubber material having a low hysteresis loss, but these rubbers may have low wet skid resistance. Thus, recently, a conjugated diene-based (co) polymer, such as a styrene-butadiene rubber (hereinafter, referred to as "SBR") or a butadiene rubber (hereinafter, referred to as "BR"), is prepared by emulsion polymerization or solution polymerization to be used as a rubber for a tire.

In a case in which the BR or SBR is used as the rubber material for a tire, the BR or SBR is typically used by being blended with a filler, such as silica or carbon black, to obtain physical properties required for a tire. However, since an affinity of the Br or SBR with the filler is poor, physical properties, such as abrasion resistance, crack resistance, or processability, may rather be reduced.

Thus, as a method of increasing dispersibility of the SBR and the filler such as silica or carbon black, a method of modifying a polymerization active site of a conjugated diene-based polymer obtained by anionic polymerization using organolithium with a functional group capable of interacting with the filler has been proposed. For example, a method of modifying a polymerization active end of a conjugated diene-based polymer with a tin-based compound or introducing an amino group, or a method of modifying with an alkoxysilane derivative has been proposed.

Also, as a method of increasing dispersibility of the BR and the filler such as silica or carbon black, a method of modifying a living active terminal with a specific coupling agent or modifier has been developed in a living polymer obtained by coordination polymerization using a catalyst composition which includes a lanthanide rare earth element compound.

However, since the BR or SBR modified by the above-described method has a low terminal modification ratio, a physical property improvement effect was insignificant with respect to a tire prepared by using the same.

DISCLOSURE OF THE INVENTION

Technical Problem

The present invention provides a modifier useful for polymer modification.

The present invention also provides a method of preparing the modifier.

The present invention also provides a modified conjugated diene-based polymer having a high modification ratio which includes a modifier-derived functional group.

The present invention also provides a method of preparing the modified conjugated diene-based polymer.

Technical Solution

According to an aspect of the present invention, there is provided a modifier represented by Formula 1.

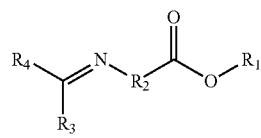

[Formula 1]

In Formula 1, $R_1$ is a monovalent hydrocarbon group having 1 to 20 carbon atoms; or a monovalent hydrocarbon group having 1 to 20 carbon atoms which includes at least one heteroatom selected from the group consisting of nitrogen (N), sulfur (S), and oxygen (O), $R_2$ is a divalent hydrocarbon group having 1 to 20 carbon atoms which is substituted or unsubstituted with at least one substituent selected from the group consisting of an alkyl group having 1 to 20 carbon atoms, a cycloalkyl group having 3 to 20 carbon atoms, and an aryl group having 6 to 30 carbon atoms; or a divalent hydrocarbon group having 1 to 20 carbon atoms which includes at least one heteroatom selected from the group consisting of N, S, and O, and $R_3$ and $R_4$ are each independently a monovalent hydrocarbon group having 1 to 20 carbon atoms which is substituted or unsubstituted with at least one substituent selected from the group consisting of an alkyl group having 1 to 20 carbon atoms, a cycloalkyl group having 3 to 20 carbon atoms, and an aryl group having 6 to 30 carbon atoms, or $R_3$ and $R_4$ are connected to each other to form an aliphatic or aromatic ring having 5 to 20 carbon atoms.

According to another aspect of the present invention, there is provided a method of preparing a modifier represented by Formula 1 which includes the steps of: performing a first reaction of a compound represented by Formula 2 and a halogen compound to prepare a salt-type compound represented by Formula 3 (step a); performing a second reaction of the salt-type compound represented by Formula 3 and an alkylamine to prepare a compound represented by Formula 4 (step b); and performing a third reaction of the compound represented by Formula 4 and an alkyl ketone compound (step c).

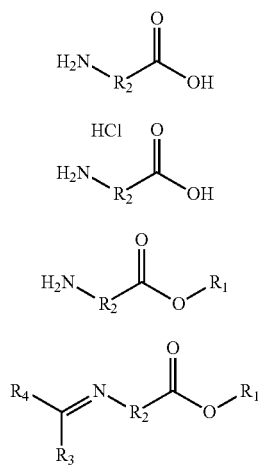

[Formula 2]

[Formula 3]

[Formula 4]

[Formula 1]

In Formulae 1 to 4, $R_1$ is a monovalent hydrocarbon group having 1 to 20 carbon atoms; or a monovalent hydrocarbon group having 1 to 20 carbon atoms which includes at least one heteroatom selected from the group consisting of N, S, and O, $R_2$ is a divalent hydrocarbon group having 1 to 20 carbon atoms which is substituted or unsubstituted with at least one substituent selected from the group consisting of an alkyl group having 1 to 20 carbon atoms, a cycloalkyl group having 3 to 20 carbon atoms, and an aryl group having 6 to 30 carbon atoms; or a divalent hydrocarbon group having 1 to 20 carbon atoms which includes at least one heteroatom selected from the group consisting of N, S, and O, and $R_3$ and $R_4$ are each independently a monovalent hydrocarbon group having 1 to 20 carbon atoms which is substituted or unsubstituted with at least one substituent selected from the group consisting of an alkyl group having 1 to 20 carbon atoms, a cycloalkyl group having 3 to 20 carbon atoms, and an aryl group having 6 to 30 carbon atoms, or $R_3$ and $R_4$ are connected to each other to form an aliphatic or aromatic ring having 5 to 20 carbon atoms.

According to another aspect of the present invention, there is provided a modified conjugated diene-based polymer including a functional group derived from the modifier represented by Formula 1.

According to another aspect of the present invention, there is provided a method of preparing the modified conjugated diene-based polymer which includes the steps of: preparing an active polymer coupled with an organometal by polymerization of a conjugated diene-based monomer in a hydrocarbon solvent in the presence of a catalyst composition including a lanthanide rare earth element-containing compound (step 1); and reacting the active polymer with the modifier represented by Formula 1 (step 2).

Advantageous Effects

Since a modifier represented by Formula 1 according to the present invention has high anionic reactivity due to the introduction of an imine group, the modifier may easily react with an active site of a polymer, and thus, modification may be easily performed.

Also, a modified conjugated diene-based polymer according to the present invention may have excellent affinity with a filler, such as carbon black, by including a function group derived from the modifier represented by Formula 1.

In addition, a method of preparing a modified conjugated diene-based polymer according to the present invention may easily prepare a modified conjugated diene-based polymer having a high modification ratio by using the modifier represented by Formula 1.

MODE FOR CARRYING OUT THE INVENTION

Hereinafter, the present invention will be described in more detail to allow for a clearer understanding of the present invention.

It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

The present invention provides a modifier useful for modification of a modified conjugated diene-based polymer.

The modifier according to an embodiment of the present invention is represented by Formula 1 below.

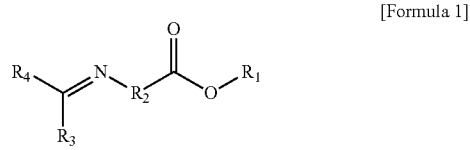

[Formula 1]

In Formula 1, $R_1$ is a monovalent hydrocarbon group having 1 to 20 carbon atoms; or a monovalent hydrocarbon group having 1 to 20 carbon atoms which includes at least one heteroatom selected from the group consisting of nitrogen (N), sulfur (S), and oxygen (O), $R_2$ is a divalent hydrocarbon group having 1 to 20 carbon atoms which is substituted or unsubstituted with at least one substituent selected from the group consisting of an alkyl group having 1 to 20 carbon atoms, a cycloalkyl group having 3 to 20 carbon atoms, and an aryl group having 6 to 30 carbon atoms; or a divalent hydrocarbon group having 1 to 20 carbon atoms which includes at least one heteroatom selected from the group consisting of N, S, and O, and $R_3$ and $R_4$ are each independently a monovalent hydrocarbon group having 1 to 20 carbon atoms which is substituted or unsubstituted with at least one substituent selected from the group consisting of an alkyl group having 1 to 20 carbon atoms, a cycloalkyl group having 3 to 20 carbon atoms, and an aryl group having 6 to 30 carbon atoms, or $R_3$ and $R_4$ are connected to each other to form an aliphatic or aromatic ring having 5 to 20 carbon atoms.

Specifically, $R_1$ in Formula 1 may be a monovalent hydrocarbon group having 1 to 20 carbon atoms, or a monovalent hydrocarbon group having 1 to 20 carbon atoms which includes at least one heteroatom selected from the group consisting of N, S, and O.

In a case in which $R_1$ is a monovalent hydrocarbon group having 1 to 20 carbon atoms, $R_1$ may be one selected from the group consisting of an alkyl group having 1 to 20 carbon atoms, a cycloalkyl group having 3 to 20 carbon atoms, an aryl group having 6 to 20 carbon atoms, and an arylalkyl group having 7 to 20 carbon atoms, and $R_1$ may specifically be one selected from the group consisting of an alkyl group having 1 to 10 carbon atoms, a cycloalkyl group having 3 to 12 carbon atoms, an aryl group having 6 to 12 carbon atoms, and an arylalkyl group having 7 to 12 carbon atoms.

Also, in a case in which $R_1$ is a monovalent hydrocarbon group having 1 to 20 carbon atoms which includes a heteroatom, $R_1$ may be one including a heteroatom instead of at least one carbon atom in the hydrocarbon group; or may be one in which at least one hydrogen atom bonded to a carbon atom in the hydrocarbon group is substituted with a heteroatom or a functional group including a heteroatom, wherein the heteroatom may be one selected from the group consisting of N, O, and S. Specifically, in a case in which $R_1$ is a monovalent hydrocarbon group having 1 to 20 carbon atoms which includes a heteroatom, $R_1$ may be an alkoxy group; a phenoxy group; a carboxy group; an acid anhydride group; an amino group; an amide group; an epoxy group; a mercapto group; $-[R^{11}O]_xR^{12}$ (where $R^{11}$ is an alkylene group having 2 to 20 carbon atoms, $R^{12}$ is selected from the group consisting of a hydrogen atom, an alkyl group having 1 to 20 carbon atoms, a cycloalkyl group having 3 to 20 carbon atoms, an aryl group having 6 to 20 carbon atoms, and an arylalkyl group having 7 to 20 carbon atoms, and x is an integer of 2 to 10); and a monovalent hydrocarbon group (e.g., hydroxyalkyl group, alkoxyalkyl group, phenoxyalkyl group, aminoalkyl group, or a thiolalkyl group) having 1 to 20 carbon atoms which includes at least one functional group selected from the group consisting of a hydroxy group, an alkoxy group, a phenoxy group, a carboxy group, an ester group, an acid anhydride group, an amino group, an amide group, an epoxy group, and a mercapto group. For example, in a case in which $R_1$ is an alkyl group having 1 to 20 carbon atoms which includes a heteroatom, $R_1$ may be one selected from the group consisting of an alkoxy group having 1 to 20 carbon atoms, an alkoxyalkyl group having 2 to 20 carbon atoms, a phenoxyalkyl group having 7 to 20 carbon atoms, an aminoalkyl group having 1 to 20 carbon atoms, and $-[R^{11}O]_xR^{12}$ (where $R^{11}$ is an alkylene group having 2 to 20 carbon atoms, $R^{12}$ is selected from the group consisting of a hydrogen atom, an alkyl group having 1 to 10 carbon atoms, a cycloalkyl group having 3 to 12 carbon atoms, an aryl group having 6 to 18 carbon atoms, and an arylalkyl group having 7 to 18 carbon atoms, and x is an integer of 2 to 10).

Furthermore, in Formula 1, $R_2$ may be a divalent hydrocarbon group having 1 to 20 carbon atoms or a divalent hydrocarbon group having 1 to 20 carbon atoms which includes at least one heteroatom selected from the group consisting of N, S, and O.

In a case in which $R_2$ is a divalent hydrocarbon group having 1 to 20 carbon atoms, $R_2$ may be an alkylene group having 1 to 10 carbon atoms such as a methylene group, an ethylene group, or a propylene group; an arylene group having 6 to 20 carbon atoms such as a phenylene group; or an arylalkylene group having 7 to 20 carbon atoms as a combination group thereof. Specifically, $R_2$ may be an alkylene group having 1 to 6 carbon atoms. Also, $R_2$ may be one substituted with at least one substituent selected from the group consisting of an alkyl group having 1 to 20 carbon atoms, a cycloalkyl group having 3 to 20 carbon atoms, and an aryl group having 6 to 30 carbon atoms.

Furthermore, in a case in which $R_2$ is a divalent hydrocarbon group having 1 to 20 carbon atoms which includes a heteroatom, $R_2$ may be one including a heteroatom instead of at least one carbon atom in the hydrocarbon group; or may be one in which at least one hydrogen atom bonded to a carbon atom in the hydrocarbon group is substituted with a heteroatom or a functional group including a heteroatom, wherein the heteroatom may be one selected from the group consisting of N, O, and S.

Specifically, in a case in which $R_2$ is a divalent hydrocarbon group having 1 to 20 carbon atoms which includes a heteroatom, $R_2$ may be a divalent hydrocarbon group having 1 to 20 carbon atoms which includes at least one functional group selected from the group consisting of an alkoxy group; a phenoxy group; a carboxy group; an acid anhydride group; an amino group; an amide group; an epoxy group; a mercapto group; a hydroxy group, an ester group.

Also, in Formula 1, $R_3$ and $R_4$ may each independently be a monovalent hydrocarbon group having 1 to 20 carbon atoms, or may be connected to each other to form an aliphatic or aromatic ring having 5 to 20 carbon atoms, and, specifically, $R_3$ and $R_4$ may each independently be an alkyl group having 1 to 10 carbon atoms which is substituted or unsubstituted with an alkyl group having 1 to 10 carbon atoms. For example, $R_3$ and $R_4$ may each independently be an alkyl group having 1 to 6 carbon atoms which is substituted or unsubstituted with an alkyl group having 1 to 5 carbon atoms.

Specifically, in the modifier of Formula 1, $R_1$ may be one selected from the group consisting of an alkyl group having 1 to 10 carbon atoms, a cycloalkyl group having 3 to 12 carbon atoms, an aryl group having 6 to 12 carbon atoms, an arylalkyl group having 7 to 12 carbon atoms, an alkoxyalkyl group having 2 to 10 carbon atoms, a phenoxyalkyl group having 7 to 12 carbon atoms, and an aminoalkyl group having 1 to 10 carbon atoms, $R_2$ may be an alkylene group having 1 to 10 carbon atoms, and $R_3$ and $R_4$ may each independently be an alkyl group having 1 to 10 carbon atoms which is substituted or unsubstituted with an alkyl group having 1 to 10 carbon atoms. For example, in Formula 1, $R_1$ may be one selected from the group consisting of an alkyl group having 1 to 10 carbon atoms, an alkoxyalkyl group having 2 to 10 carbon atoms, and a phenoxyalkyl group having 7 to 12 carbon atoms, $R_2$ may be an alkylene group having 1 to 6 carbon atoms, and $R_3$ and $R_4$ may each independently be an alkyl group having 1 to 6 carbon atoms which is substituted or unsubstituted with an alkyl group having 1 to 5 carbon atoms.

Specifically, the modifier represented by Formula 1 may include those represented by the following Formulae 1-1 to 1-4.

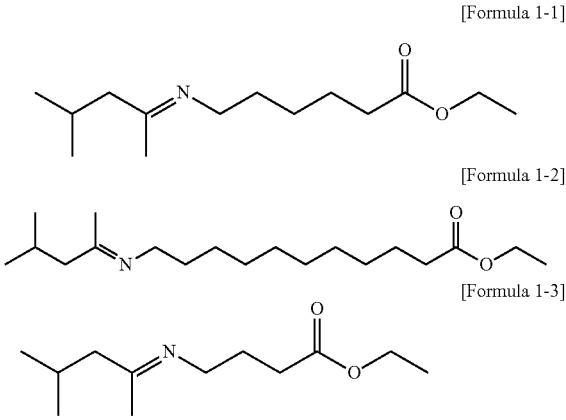

[Formula 1-4]

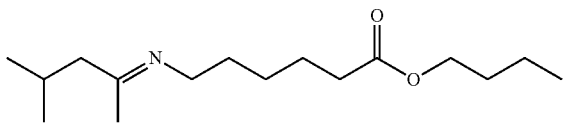

Also, the modifier may have a solubility in 100 g of a non-polar solvent, for example, hexane, of 10 g or more at 25° C. and 1 atmosphere. Herein, the solubility of the modifier denotes a degree to which the modifier is clearly dissolved without a turbidity phenomenon during visual observation. Since the modifier has high solubility as described above, a high modification ratio for the polymer may be achieved.

The modifier represented by Formula 1 according to the present invention may easily modify a conjugated diene-based polymer at a high modification ratio by including a reactive functional group for the conjugated diene-based polymer, a filler affinity functional group, and a solvent affinity functional group, and may improve abrasion resistance, low fuel consumption property, and processability of a rubber composition including the polymer and a molded article, such as a tire, prepared therefrom. Specifically, the modifier of Formula 1 may include an imine group and an aliphatic hydrocarbon group in the molecule as described above, and, since the imine group may modify the conjugated diene-based polymer at a high modification ratio by having a high reactivity with an active site of the conjugated diene-based polymer, the functional group substituted with the modifier may be introduced into the conjugated diene-based polymer in a high yield. Also, the imine group may further improve affinity with a filler, particularly, carbon black, while reacting with a conjugated diene-based polymer end to be converted to a secondary amino group. Furthermore, the aliphatic hydrocarbon group, particularly, a linear aliphatic hydrocarbon group may increase solubility of the modifier by improving affinity with a polymerization solvent, and thus, may improve a modification ratio with respect to the conjugated diene-based polymer. In addition, in the modifier, the hydrocarbon group including a heteroatom, specifically, a tertiary amino group may improve affinity of the modified conjugated diene-based polymer with the filler in the rubber composition. For example, since the tertiary amino group may prevent agglomeration of the filler by disturbing a hydrogen bond between hydroxide groups present on the surface of the filler, the tertiary amino group may improve dispersibility of the filler in the rubber composition.

Furthermore, the present invention provides a method of preparing the modifier represented by Formula 1.

The method of preparing the modifier according to an embodiment of the present invention includes the steps of: performing a first reaction of a compound represented by Formula 2 and a halogen compound to prepare a salt-type compound represented by Formula 3 (step a); performing a second reaction of the salt-type compound represented by Formula 3 and an alkylamine to prepare a compound represented by Formula 4 (step b); and performing a third reaction of the compound represented by Formula 4 and an alkyl ketone compound (step c).

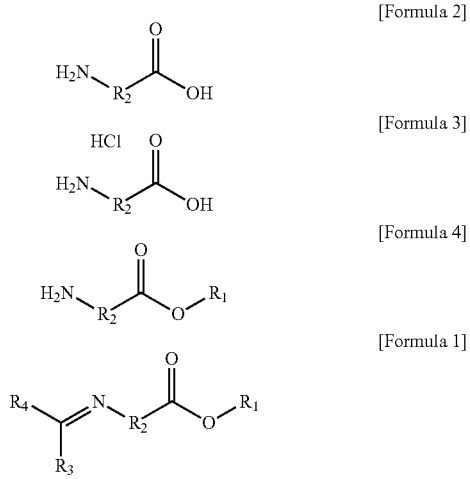

In Formulae 1 to 4, $R_1$ is a monovalent hydrocarbon group having 1 to 20 carbon atoms; or a monovalent hydrocarbon group having 1 to 20 carbon atoms which includes at least one heteroatom selected from the group consisting of N, S, and O, $R_2$ is a divalent hydrocarbon group having 1 to 20 carbon atoms which is substituted or unsubstituted with at least one substituent selected from the group consisting of an alkyl group having 1 to 20 carbon atoms, a cycloalkyl group having 3 to 20 carbon atoms, and an aryl group having 6 to 30 carbon atoms; or a divalent hydrocarbon group having 1 to 20 carbon atoms which includes at least one heteroatom selected from the group consisting of N, S, and O, and $R_3$ and $R_4$ are each independently a monovalent hydrocarbon group having 1 to 20 carbon atoms which is substituted or unsubstituted with at least one substituent selected from the group consisting of an alkyl group having 1 to 20 carbon atoms, a cycloalkyl group having 3 to 20 carbon atoms, and an aryl group having 6 to 30 carbon atoms, or $R_3$ and $R_4$ are connected to each other to form an aliphatic or aromatic ring having 5 to 20 carbon atoms.

The first reaction of step a is a step for preparing a salt-type compound represented by Formula 3, wherein the first reaction may be performed by reacting a compound represented by Formula 2 with a halogen compound.

Also, the second reaction of step b is a step for preparing a compound represented by Formula 4, wherein the second reaction may be performed by reacting the salt-type compound represented by Formula 3 with an alkylamine. In this case, the first reaction of step a and the second reaction of step b may be continuously performed in one reactor or may be stepwise performed in two reactors.

The first reaction and the second reaction may be respectively performed in the presence of a polar solvent at low temperature. In this case, in the first reaction, the compound represented by Formula 2 and the halogen compound may be used in a stoichiometric ratio, and, specifically, the compound represented by Formula 2 and the halogen compound may be used at a molar ratio of 1:0.9 to 1:1. Also, in the second reaction, the salt-type compound represented by Formula 3 and the alkylamine may be used in a stoichiometric ratio, and, specifically, the salt-type compound represented by Formula 3 and the alkylamine may be used at a molar ratio of 1:1.5 to 1:3.

Herein, the low temperature in the first reaction and the second reaction may each independently be in a temperature range of −10° C. to 25° C., and the first reaction and the second reaction may be performed at the same temperature or may be performed at different temperatures.

Furthermore, the polar solvent used in the first reaction and the second reaction may each independently be at least one selected from methanol, ethanol, butanol, hexanol, and dichloromethane.

Specifically, the polar solvent used in the first reaction may have relatively stronger polarity than the polar solvent used in the second reaction, wherein the polar solvent used in the first reaction may particularly be at least one selected from methanol, ethanol, butanol, and hexanol, and may more particularly be ethanol, and the polar solvent used in the second reaction may be dichloromethane.

Also, the halogen compound is not particularly limited, but, for example, may be thionyl chloride.

Furthermore, the alkylamine is not particularly limited, but, for example, may be triethylamine.

The third reaction of step c is a step for preparing the modifier represented by Formula 1, wherein the third reaction may be performed by reacting a compound represented by Formula 4 with an alkyl ketone compound. In this case, the third reaction may be performed at high temperature, and the compound represented by Formula 4 and the alkyl ketone compound may be used in a stoichiometric ratio.

Specifically, the third reaction may be performed in a temperature range of 100° C. to 150° C., and the compound represented by Formula 4 and the alkyl ketone compound may be used at a molar ratio of 1:1 to 1:5.

Also, the alkyl ketone compound is not particularly limited, but, for example, may be at least one selected from the group consisting of methyl isopropyl ketone, methyl isobutyl ketone, cyclohexanone, methyl ethyl ketone, diisopropyl ketone, ethyl butyl ketone, methyl butyl ketone, and dipropyl ketone.

In addition, the present invention provides a modified conjugated diene-based polymer including a functional group derived from a modifier represented by Formula 1 below.

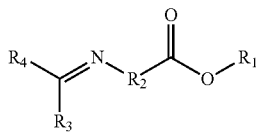

[Formula 1]

In Formula 1, $R_1$ is a monovalent hydrocarbon group having 1 to 20 carbon atoms; or a monovalent hydrocarbon group having 1 to 20 carbon atoms which includes at least one heteroatom selected from the group consisting of N, S, and O, $R_2$ is a divalent hydrocarbon group having 1 to 20 carbon atoms which is substituted or unsubstituted with at least one substituent selected from the group consisting of an alkyl group having 1 to 20 carbon atoms, a cycloalkyl group having 3 to 20 carbon atoms, and an aryl group having 6 to 30 carbon atoms; or a divalent hydrocarbon group having 1 to 20 carbon atoms which includes at least one heteroatom selected from the group consisting of N, S, and O, and $R_3$ and $R_4$ are each independently a monovalent hydrocarbon group having 1 to 20 carbon atoms which is substituted or unsubstituted with at least one substituent selected from the group consisting of an alkyl group having 1 to 20 carbon atoms, a cycloalkyl group having 3 to 20 carbon atoms, and an aryl group having 6 to 30 carbon atoms, or $R_3$ and $R_4$ are connected to each other to form an aliphatic or aromatic ring having 5 to 20 carbon atoms.

The modified conjugated diene-based polymer according to an embodiment of the present invention may be prepared by reacting an active polymer coupled with an organometal with the modifier represented by Formula 1 through a preparation method to be described later, and physical properties of the modified conjugated diene-based polymer may be improved by including the functional group derived from the modifier represented by Formula 1.

Specifically, the modifier represented by Formula 1 may be the same as described above.

Specifically, the modified conjugated diene-based polymer may include a filler affinity functional group and a solvent affinity functional group by including the functional group derived from the modifier represented by Formula 1, and thus, abrasion resistance, low fuel consumption property, and processability of a rubber composition including the modified conjugated diene-based polymer and a molded article, such as a tire, prepared therefrom may be improved.

The modified conjugated diene-based polymer may have a number-average molecular weight (Mn) of 100,000 g/mol to 700,000 g/mol, for example, 120,000 g/mol to 500,000 g/mol.

Also, the modified conjugated diene-based polymer may have a weight-average molecular weight (Mw) of 300,000 g/mol to 1,200,000 g/mol, for example, 400,000 g/mol to 1,000,000 g/mol.

Furthermore, the modified conjugated diene-based polymer may have a molecular weight distribution (Mw/Mn) of 1.05 to 5.

In addition, in consideration of an improvement in balance between mechanical properties, an elastic modulus, and processability of the rubber composition when the modified conjugated diene-based polymer according to the embodiment of the present invention is used in the rubber composition, the weight-average molecular weight and the number-average molecular weight may satisfy the above-described ranges at the same time while the modified conjugated diene-based polymer has the above-described molecular weight distribution range.

Specifically, the modified conjugated diene-based polymer may have a molecular weight distribution of 3.4 or less, a weight-average molecular weight of 300,000 g/mol to 1,200,000 g/mol, and a number-average molecular weight of 100,000 g/mol to 700,000 g/mol, and, for example, may have a polydispersity of 3.2 or less, a weight-average molecular weight of 400,000 g/mol to 1,000,000 g/mol, and a number-average molecular weight of 120,000 g/mol to 500,000 g/mol.

Herein, each of the weight-average molecular weight and the number-average molecular weight is a polystyrene-equivalent molecular weight analyzed by gel permeation chromatography (GPC), and the molecular weight distribution (Mw/Mn) is also known as polydispersity, wherein it was calculated as a ratio (Mw/Mn) of the weight-average molecular weight (Mw) to the number-average molecular weight (Mn).

Also, the modified conjugated diene-based polymer according to the embodiment of the present invention may be a polymer having high linearity in which a value of −S/R (stress/relaxation) at 100° C. is 0.7 or more. In this case, the −S/R denotes a change in stress in response to the same amount of strain generated in a material, wherein it is an index indicating linearity of a polymer. Normally, the linearity of the polymer is low as the −S/R value is reduced, and rolling resistance or rotation resistance when the polymer is used in the rubber composition is increased as the linearity is reduced. Furthermore, branching degree and molecular weight distribution of the polymer may be estimated from the −S/R value, and the higher the −S/R value is, the higher the branching degree is and the wider the molecular weight distribution is. As a result, processability of the polymer is excellent, but mechanical properties are low.

Since the modified conjugated diene-based polymer according to the embodiment of the present invention has a high −S/R value of 0.7 or more at 100° C. as described above, resistance characteristics and fuel consumption property may be excellent when used in the rubber composition. Specifically, the −S/R value of the modified conjugated diene-based polymer may be in a range of 0.7 to 1.0.

Herein, the −S/R value was measured with a large rotor at a rotor speed of 2±0.02 rpm at 100° C. using a Mooney viscometer, for example, MV2000E by Monsanto Company. Specifically, after the polymer was left standing for 30 minutes or more at room temperature (23±3° C.), 27±3 g of the polymer was taken and filled into a die cavity, and Mooney viscosity was measured while applying a torque by operating a platen. Then, the −S/R value was obtained by measuring a slope of change in the Mooney viscosity obtained while the torque was released for additional 1 minute.

Also, specifically, the modified conjugated diene-based polymer may have a cis-1,4 bond content of a conjugated diene portion, which is measured by Fourier transform infrared spectroscopy (FT-IR), of 95% or more, for example, 98% or more. Thus, abrasion resistance, crack resistance, and ozone resistance of the rubber composition may be improved when used in the rubber composition.

Furthermore, the modified conjugated diene-based polymer may have a vinyl content of the conjugated diene portion, which is measured by Fourier transform infrared spectroscopy, of 5% or less, for example, 2% or less. In a case in which the vinyl content in the polymer is greater than 5%, the abrasion resistance, crack resistance, and ozone resistance of the rubber composition including the same may be deteriorated.

Herein, the cis-1,4 bond content and vinyl content in the polymer are measured by the Fourier transform infrared spectroscopy (FT-IR) in which, after measuring a FT-IR transmittance spectrum of a carbon disulfide solution of the conjugated diene-based polymer which is prepared at a concentration of 5 mg/mL by using disulfide carbon of the same cell as a blank, each content was obtained by using a maximum peak value (a, base line) near 1,130 cm$^{-1}$ of the measurement spectrum, a minimum value (b) near 967 cm$^{-1}$ which indicates a trans-1,4 bond, a minimum value (c) near 911 cm$^{-1}$ which indicates a vinyl bond, and a minimum value (d) near 736 cm$^{-1}$ which indicates a cis-1,4 bond.

In addition, the present invention provides a method of preparing a modified conjugated diene-based polymer including a functional group derived from the modifier represented by Formula 1.

The preparation method according to an embodiment of the present invention includes the steps of: preparing an active polymer coupled with an organometal by polymerization of a conjugated diene-based monomer in a hydrocarbon solvent in the presence of a catalyst composition including a lanthanide rare earth element-containing compound (step 1); and reacting the active polymer with a modifier represented by Formula 1 (step 2)

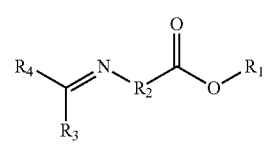

[Formula 1]

In Formula 1, $R_1$ is a monovalent hydrocarbon group having 1 to 20 carbon atoms; or a monovalent hydrocarbon group having 1 to 20 carbon atoms which includes at least one heteroatom selected from the group consisting of N, S, and O, $R_2$ is a divalent hydrocarbon group having 1 to 20 carbon atoms which is substituted or unsubstituted with at least one substituent selected from the group consisting of an alkyl group having 1 to 20 carbon atoms, a cycloalkyl group having 3 to 20 carbon atoms, and an aryl group having 6 to 30 carbon atoms; or a divalent hydrocarbon group having 1 to 20 carbon atoms which includes at least one heteroatom selected from the group consisting of N, S, and O, and $R_3$ and $R_4$ are each independently a monovalent hydrocarbon group having 1 to 20 carbon atoms which is substituted or unsubstituted with at least one substituent selected from the group consisting of an alkyl group having 1 to 20 carbon atoms, a cycloalkyl group having 3 to 20 carbon atoms, and an aryl group having 6 to 30 carbon atoms, or $R_3$ and $R_4$ are connected to each other to form an aliphatic or aromatic ring having 5 to 20 carbon atoms.

Specifically, the modifier represented by Formula 1 may be the same as described above.

Step 1 is a step for preparing an active polymer coupled with an organometal by using a catalyst composition including a lanthanide rare earth element-containing compound, wherein step 1 may be performed by polymerization of a conjugated diene-based monomer in a hydrocarbon solvent in the presence of the catalyst composition.

The conjugated diene-based monomer is not particularly limited, but, for example, may be at least one selected from the group consisting of 1,3-butadiene, 2,3-dimethyl-1,3-butadiene, piperylene, 3-butyl-1,3-octadiene, isoprene, and 2-phenyl-1,3-butadiene.

The hydrocarbon solvent is not particularly limited, but, for example, may be at least one selected from the group consisting of n-pentane, n-hexane, n-heptane, isooctane, cyclohexane, toluene, benzene, and xylene.

The catalyst composition may be used in an amount such that the lanthanide rare earth element-containing compound is included in an amount of 0.1 mmol to 0.5 mmol based on total 100 g of the conjugated diene-based monomer, and may specifically be used in an amount such that the lanthanide rare earth element-containing compound is included in an amount of 0.1 mmol to 0.4 mmol, for example, 0.1 mmol to 0.25 mmol, based on total 100 g of the conjugated diene-based monomer. Since the preparation method according to the embodiment of the present invention uses the catalyst composition within the above range, catalytic activity is high and an appropriate catalyst concentration is provided, and thus, it is not necessary to carry out a separate demineralization process.

The lanthanide rare earth element-containing compound is not particularly limited, but, for example, may be at least one compound of rare earth metals with an atomic number of 57 to 71, such as lanthanum, neodymium, cerium, gadolinium, or praseodymium, and may specifically be a compound including at least one selected from the group consisting of neodymium, lanthanum, and gadolinium.

Also, the lanthanide rare earth element-containing compound may include carboxylates containing the above-described rare earth element (e.g., neodymium acetate, neodymium acrylate, neodymium methacrylate, neodymium gluconate, neodymium citrate, neodymium fumarate, neodymium lactate, neodymium maleate, neodymium oxalate, neodymium 2-ethylhexanoate, or neodymium neodecanoate); organophosphates containing the above-described rare earth element (e.g., neodymium dibutyl phosphate, neodymium dipentyl phosphate, neodymium dihexyl phosphate, neodymium diheptyl phosphate, neodymium dioctyl phosphate, neodymium bis(1-methylheptyl) phosphate, neodymium bis(2-ethylhexyl) phosphate, or neodymium didecyl phosphate); organophosphonates containing the above-described rare earth element (e.g., neodymium butyl phosphonate, neodymium pentyl phosphonate, neodymium hexyl phosphonate, neodymium heptyl phosphonate, neodymium octyl phosphonate, neodymium (1-methylheptyl) phosphonate, neodymium (2-ethylhexyl) phosphonate, neodymium decyl phosphonate, neodymium dodecyl phosphonate, or neodymium octadecyl phosphonate); organophosphinates containing the above-described rare earth element (e.g., neodymium butylphosphinate, neodymium pentylphosphinate, neodymium hexylphosphinate, neodymium heptylphosphinate, neodymium octylphosphinate, neodymium (1-methylheptyl)phosphinate, or neodymium (2-ethylhexyl)phosphinate); carbamates containing the above-described rare earth element (e.g., neodymium dimethylcarbamate, neodymium diethylcarbamate, neodymium diisopropylcarbamate, neodymium dibutylcarbamate, or neodymium dibenzylcarbamate); dithiocarbamates containing the above-described rare earth element (e.g., neodymium dimethyldithiocarbamate, neodymium diethyldithiocarbamate, neodymium diisopropyldithiocarbamate, or neodymium dibutyldithiocarbamate); xanthates containing the above-described rare earth element (e.g., neodymium methylxanthate, neodymium ethylxanthate, neodymium isopropylxanthate, neodymium butylxanthate, or neodymium benzylxanthate); R-diketonates containing the above-described rare earth element (e.g., neodymium acetylacetonate, neodymium trifluoroacetylacetonate, neodymium hexafluoroacetylacetonate, or neodymium benzoylacetonate); alkoxides or aryloxides containing the above-described rare earth element (e.g., neodymium methoxide, neodymium ethoxide, neodymium isopropoxide, neodymium phenoxide, or neodymium nonylphenoxide); halides or pseudo-halides containing the above-described rare earth element (e.g., neodymium fluoride, neodymium chloride, neodymium bromide, neodymium iodide, neodymium cyanide, neodymium cyanate, neodymium thiocyanate, or neodymium azide); oxyhalides containing the above-described rare earth element (e.g., neodymium oxyfluoride, neodymium oxychloride, or neodymium oxybromide); or organolanthanide rare earth element-containing compounds including at least one rare earth element-carbon bond (e.g., Cp$_3$Ln, Cp$_2$LnR, Cp$_2$LnCl, CpLnCl$_2$, CpLn(cyclooctatetraene), (C$_5$Me$_5$)$_2$LnR, LnR$_3$, Ln(allyl)$_3$, or Ln(allyl)$_2$Cl, where Ln represents a rare earth metal element, and R represents a hydrocarbyl group), and may include any one thereof or a mixture of two or more thereof.

Specifically, the lanthanide rare earth element-containing compound may include a neodymium-based compound represented by Formula 5 below.

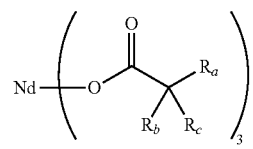

[Formula 5]

In Formula 5, $R_a$ to $R_c$ may each independently be hydrogen or an alkyl group having 1 to 12 carbon atoms, but all of $R_a$ to $R_c$ are not hydrogen at the same time.

As a specific example, the neodymium-based compound may be at least one selected from the group consisting of Nd(neodecanoate)$_3$, Nd(2-ethylhexanoate)$_3$, Nd(2,2-diethyl decanoate)$_3$, Nd(2,2-dipropyl decanoate)$_3$, Nd(2,2-dibutyl decanoate)$_3$, Nd(2,2-dihexyl decanoate)$_3$, Nd(2,2-dioctyl decanoate)$_3$, Nd(2-ethyl-2-propyl decanoate)$_3$, Nd(2-ethyl-2-butyl decanoate)$_3$, Nd(2-ethyl-2-hexyl decanoate)$_3$, Nd(2-propyl-2-butyl decanoate)$_3$, Nd (2-propyl-2-hexyl decanoate)$_3$, Nd(2-propyl-2-isopropyl decanoate)$_3$, Nd(2-butyl-2-hexyl decanoate)$_3$, Nd(2-hexyl-2-octyl decanoate)$_3$, Nd(2-t-butyl decanoate)$_3$, Nd(2,2-diethyl octanoate)$_3$, Nd(2,2-dipropyl octanoate)$_3$, Nd(2,2-dibutyl octanoate)$_3$, Nd(2,2-dihexyl octanoate)$_3$, Nd(2-ethyl-2-propyl octanoate)$_3$, Nd(2-ethyl-2-hexyl octanoate)$_3$, Nd(2,2-diethyl nonanoate)$_3$, Nd(2,2-dipropyl nonanoate)$_3$, Nd(2,2-dibutyl nonanoate)$_3$, Nd(2,2-dihexyl nonanoate)$_3$, Nd(2-ethyl-2-propyl nonanoate)$_3$, and Nd(2-ethyl-2-hexyl nonanoate)$_3$.

As another example, in consideration of excellent solubility in the polymerization solvent without a concern for oligomerization, a rate of conversion to a catalytically active species, and the resulting excellent catalytic activity improvement effect, the lanthanide rare earth element-containing compound may specifically be a neodymium-based compound in which, in Formula 5, $R_a$ is a linear or branched alkyl group having 4 to 12 carbon atoms, and $R_b$ and $R_c$ are each independently hydrogen or an alkyl group having 2 to 8 carbon atoms, but $R_b$ and $R_c$ are not hydrogen at the same time.

As a specific example, in Formula 5, $R_a$ may be a linear or branched alkyl group having 6 to 8 carbon atoms, and $R_b$ and $R_c$ may each independently be hydrogen or an alkyl group having 2 to 6 carbon atoms, wherein $R_b$ and $R_c$ may not be hydrogen at the same time, specific examples of the neodymium-based compound may be at least one selected from the group consisting of Nd(2,2-diethyl decanoate)$_3$, Nd(2,2-dipropyl decanoate)$_3$, Nd(2,2-dibutyl decanoate)$_3$, Nd(2,2-dihexyl decanoate)$_3$, Nd(2,2-dioctyl decanoate)$_3$, Nd(2-ethyl-2-propyl decanoate)$_3$, Nd(2-ethyl-2-butyl decanoate)$_3$, Nd(2-ethyl-2-hexyl decanoate)$_3$, Nd(2-propyl-2-butyl decanoate)$_3$, Nd(2-propyl-2-hexyl decanoate)$_3$, Nd(2-propyl-2-isopropyl decanoate)$_3$, Nd(2-butyl-2-hexyl decanoate)$_3$, Nd(2-hexyl-2-octyl decanoate)$_3$, Nd(2-t-butyl decanoate)$_3$, Nd(2,2-diethyl octanoate)$_3$, Nd(2,2-dipropyl octanoate)$_3$, Nd(2,2-dibutyl octanoate)$_3$, Nd(2,2-dihexyl octanoate)$_3$, Nd(2-ethyl-2-propyl octanoate)$_3$, Nd(2-ethyl-2-hexyl octanoate)$_3$, Nd(2,2-diethyl nonanoate)$_3$, Nd(2,2-dipropyl nonanoate)$_3$, Nd(2,2-dibutyl nonanoate)$_3$, Nd(2,2-dihexyl nonanoate)$_3$, Nd(2-ethyl-2-propyl nonanoate)$_3$, and Nd(2-ethyl-2-hexyl nonanoate)$_3$, and, among them, the neodymium-based compound may be at least one selected from the group consisting of Nd(2,2-diethyl decanoate)$_3$, Nd(2,2-dipropyl decanoate)$_3$, Nd(2,2-dibutyl decanoate)$_3$, Nd(2,2-dihexyl decanoate)$_3$, and Nd(2,2-dioctyl decanoate)$_3$.

Specifically, in Formula 5, $R_a$ may be a linear or branched alkyl group having 6 to 8 carbon atoms, and $R_b$ and $R_c$ may each independently be an alkyl group having 2 to 6 carbon atoms.

As described above, since the neodymium-based compound represented by Formula 5 includes a carboxylate ligand including alkyl groups of various lengths having 2 or more carbon atoms as a substituent at an α (alpha) position, coagulation of the compound may be blocked by inducing steric changes around the neodymium center metal, and accordingly, oligomerization may be suppressed. Also, with respect to the neodymium-based compound, since a ratio of neodymium located in a center portion, which has high solubility in the polymerization solvent and has difficulties in conversion to the catalytically active species, is reduced, the rate of conversion to the catalytically active species is high.

Furthermore, the lanthanide rare earth element-containing compound according to an embodiment of the present invention may have a solubility of about 4 g or more per 6 g of a non-polar solvent at room temperature (25° C.).

In the present invention, the solubility of the neodymium-based compound denotes a degree to which the neodymium-based compound is clearly dissolved without a turbidity phenomenon, wherein since the neodymium-based compound has high solubility as described above, excellent catalytic activity may be achieved.

Also, the lanthanide rare earth element-containing compound according to the embodiment of the present invention may be used in the form of a reactant with a Lewis base. The reactant may improve the solubility of the lanthanide rare earth element-containing compound in the solvent and may be stored in a stable state for a long period of time by the Lewis base. The Lewis base, for example, may be used in a ratio of 30 mol or less or 1 mole to 10 mol per 1 mol of the rare earth element. Examples of the Lewis base may be acetylacetone, tetrahydrofuran, pyridine, N,N'-dimethylformamide, thiophene, diphenyl ether, triethylamine, an organic phosphorus compound, or a monohydric or dihydric alcohol.

The catalyst composition may further include at least one of (a) alkylating agent, (b) halide, and (c) conjugated diene-based monomer, in addition to the lanthanide rare earth element-containing compound.

Hereinafter, (a) alkylating agent, (b) halide, and (c) conjugated diene-based monomer will be separately described in detail.

(a) Alkylating Agent

The alkylating agent is an organometallic compound that may transfer a hydrocarbyl group to another metal, wherein it may act as a cocatalyst composition. The alkylating agent may be used without particular limitation as long as it is commonly used as an alkylating agent during the preparation of a diene-based polymer, and, for example, may be an organometallic compound, which is soluble in the polymerization solvent and contains a metal-carbon bond, such as an organoaluminum compound, an organomagnesium compound, or an organolithium compound.

Specifically, the organoaluminum compound may include alkylaluminum such as trimethylaluminum, triethylaluminum, tri-n-propylaluminum, triisopropylaluminum, tri-n-butylaluminum, triisobutylaluminum, tri-t-butylaluminum, tripentylaluminum, trihexylaluminum, tricyclohexylaluminum, or trioctylaluminum; dihydrocarbylaluminum hydride such as diethylaluminum hydride, di-n-propylaluminum hydride, diisopropylaluminum hydride, di-n-butylaluminum hydride, diisobutylaluminum hydride (DIBAH), di-n-octylaluminum hydride, diphenylaluminum hydride, di-p-tolylaluminum hydride, dibenzylaluminum hydride, phenylethylaluminum hydride, phenyl-n-propylaluminum hydride, phenylisopropylaluminum hydride, phenyl-n-butylaluminum hydride, phenylisobutylaluminum hydride, phenyl-n-octylaluminum hydride, p-tolylethylaluminum hydride, p-tolyl-n-propylaluminum hydride, p-tolylisopropylaluminum hydride, p-tolyl-n-butylaluminum hydride, p-tolylisobutylaluminum hydride, p-tolyl-n-octylaluminum hydride, benzylethylaluminum hydride, benzyl-n-propylaluminum hydride, benzylisopropylaluminum hydride, benzyl-n-butylaluminum hydride, benzylisobutylaluminum hydride, or benzyl-n-octylaluminum hydride; and hydrocarbylaluminum dihydride such as ethylaluminum dihydride, n-propylaluminum dihydride, isopropylaluminum dihydride, n-butylaluminum dihydride, isobutylaluminum dihydride, or n-octylaluminum dihydride. The organomagnesium compound may include an alkyl magnesium compound such as diethylmagnesium, di-n-propylmagnesium, diisopropylmagnesium, dibutylmagnesium, dihexylmagnesium, diphenylmagnesium, or dibenzylmagnesium, and the organolithium compound may include an alkyl lithium compound such as n-butyllithium.

Also, the organoaluminum compound may be aluminoxane.

The aluminoxane may be prepared by reacting a trihydrocarbylaluminum-based compound with water, and may specifically be linear aluminoxane of the following Formula 6a or cyclic aluminoxane of the following Formula 6b.

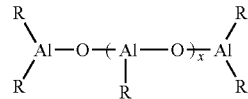

[Formula 6a]

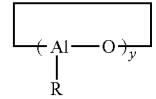

[Formula 6b]

In Formulae 6a and 6b, R is a monovalent organic group bonded to an aluminum atom through a carbon atom, wherein R may be a hydrocarbyl group, and x and y may each independently be an integer of 1 or more, particularly 1 to 100, and more particularly 2 to 50.

For example, the aluminoxane may include methylaluminoxane (MAO), modified methylaluminoxane (MMAO), ethylaluminoxane, n-propylaluminoxane, isopropylaluminoxane, butylaluminoxane, isobutylaluminoxane, n-pentylaluminoxane, neopentylaluminoxane, n-hexylaluminoxane, n-octylaluminoxane, 2-ethylhexylaluminoxane, cylcohexylaluminoxane, 1-methylcyclopentylaluminoxane, phenylaluminoxane, or 2,6-dimethylphenylaluminoxane, and any one thereof or a mixture of two or more thereof may be used.

Furthermore, the modified methylaluminoxane may be one in which a methyl group of methylaluminoxane is substituted with a formula group (R), specifically, a hydrocarbon group having 2 to 20 carbon atoms, wherein the modified methylaluminoxane may specifically be a compound represented by Formula 7 below.

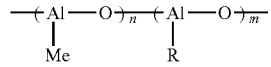

[Formula 7]

In Formula 7, R is the same as defined above, and m and n may each independently be an integer of 2 or more. Also, in Formula 7, Me represents a methyl group.

Specifically, in Formula 7, R may be an alkyl group having 2 to 20 carbon atoms, a cycloalkyl group having 3 to 20 carbon atoms, an alkenyl group having 2 to 20 carbon atoms, a cycloalkenyl group having 3 to 20 carbon atoms, an aryl group having 6 to 20 carbon atoms, an arylalkyl group having 7 to 20 carbon atoms, an alkylaryl group having 7 to 20 carbon atoms, an allyl group, or an alkynyl group having 2 to 20 carbon atoms, may particularly be an alkyl group having 2 to 10 carbon atoms such as an ethyl group, an isobutyl group, a hexyl group, or an octyl group, and may more particularly be an isobutyl group.

Specifically, the modified methylaluminoxane may be one in which about 50 mol % to 90 mol % of the methyl group of the methylaluminoxane is substituted with the above-described hydrocarbon group. When the amount of the hydrocarbon group substituted in the modified methylaluminoxane is within the above range, the modified methylaluminoxane may increase catalytic activity by promoting alkylation.

The modified methylaluminoxane may be prepared by a conventional method, and may specifically be prepared by using trimethylaluminum and alkylaluminum other than trimethylaluminum. In this case, the alkylaluminum may be triisopropylaluminum, triethylaluminum, trihexylaluminum, or trioctylaluminum, and any one thereof or a mixture of two or more thereof may be used.

Also, the catalyst composition according to an embodiment of the present invention may include the alkylating agent at a molar ratio of 1 to 200, particularly 1 to 100, and more particularly 3 to 20 based on 1 mol of the lanthanide rare earth element-containing compound. In a case in which the alkylating agent is included at a molar ratio of greater than 200, catalytic reaction control is not easy during the preparation of the polymer, and an excessive amount of the alkylating agent may cause a side reaction.

(b) Halide

The halide is not particularly limited, but, for example, may include elemental halogen, an interhalogen compound, halogenated hydrogen, an organic halide, a non-metal halide, a metal halide, or an organic metal halide, and any one thereof or a mixture of two or more thereof may be used. Among them, in consideration of catalytic activity enhancement and the resulting significant improvement in reactivity, any one selected from the group consisting of an organic halide, a metal halide, and an organic metal halide, or a mixture of two or more thereof may be used as the halide.

The elemental halogen may include fluorine, chlorine, bromine, or iodine.

Also, the interhalogen compound may include iodine monochloride, iodine monobromide, iodine trichloride, iodine pentafluoride, iodine monofluoride, or iodine trifluoride.

Furthermore, the halogenated hydrogen may include hydrogen fluoride, hydrogen chloride, hydrogen bromide, or hydrogen iodide.

Also, the organic halide may include t-butyl chloride (t-BuCl), t-butyl bromide, allyl chloride, allyl bromide, benzyl chloride, benzyl bromide, chloro-di-phenylmethane, bromo-di-phenylmethane, triphenylmethyl chloride, triphenylmethyl bromide, benzylidene chloride, benzyliene bromide, methyltrichlorosilane, phenyltrichlorosilane, dimethyldichlorosilane, diphenyldichlorosilane, trimethylchlorosilane (TMSCl), benzoyl chloride, benzoyl bromide, propionyl chloride, propionyl bromide, methyl chloroformate, methyl bromoformate, iodomethane, diiodomethane, triiodomethane (also referred to as 'iodoform'), tetraiodomethane, 1-iodopropane, 2-iodopropane, 1,3-diiodopropane, t-butyl iodide, 2,2-dimethyl-1-iodopropane (also referred to as 'neopentyl iodide'), allyl iodide, iodobenzene, benzyl iodide, diphenylmethyl iodide, triphenylmethyl iodide, benzylidene iodide (also referred to as 'benzal iodide'), trimethylsilyl iodide, triethylsilyl iodide, triphenylsilyl iodide, dimethyldiiodosilane, diethyldiiodosilane, diphenyldiiodosilane, methyltriiodosilane, ethyltriiodosilane, phenyltriiodosilane, benzoyl iodide, propionyl iodide, or methyl iodoformate.

Furthermore, the non-metal halide may include phosphorous trichloride, phosphorous tribromide, phosphorous pentachloride, phosphorous oxychloride, phosphorous oxybromide, boron trifluoride, boron trichloride, boron tribromide, silicon tetrafluoride, silicon tetrachloride ($SiCl_4$), silicon tetrabromide, arsenic trichloride, arsenic tribromide, selenium tetrachloride, selenium tetrabromide, tellurium tetrachloride, tellurium tetrabromide, silicon tetraiodide, arsenic triiodide, tellurium tetraiodide, boron triiodide, phosphorous triiodide, phosphorous oxyiodide, or selenium tetraiodide.

Also, the metal halide may include tin tetrachloride, tin tetrabromide, aluminum trichloride, aluminum tribromide, antimony trichloride, antimony pentachloride, antimony tribromide, aluminum trifluoride, gallium trichloride, gallium tribromide, gallium trifluoride, indium trichloride, indium tribromide, indium trifluoride, titanium tetrachloride, titanium tetrabromide, zinc dichloride, zinc dibromide, zinc difluoride, aluminum triiodide, gallium triiodide, indium triiodide, titanium tetraiodide, zinc diiodide, germanium tetraiodide, tin tetraiodide, tin diiodide, antimony triiodide, or magnesium diiodide.

Furthermore, the organic metal halide may include dimethylaluminum chloride, diethylaluminum chloride, dimethylaluminum bromide, diethylaluminum bromide, dimethylaluminum fluoride, diethylaluminum fluoride, methylaluminum dichloride, ethylaluminum dichloride, methylaluminum dibromide, ethylaluminum dibromide, methylaluminum difluoride, ethylaluminum difluoride, methylaluminum sesquichloride, ethylaluminum sesquichloride (EASC), isobutylaluminum sesquichloride, methylmagnesium chloride, methylmagnesium bromide, ethylmagnesium chloride, ethylmagnesium bromide, n-butylmagnesium chloride, n-butylmagnesium bromide, phenylmagnesium chloride, phenylmagnesium bromide, benzylmagnesium chloride, trimethyltin chloride, trimethyltin bromide, triethyltin chloride, triethyltin bromide, di-t-butyltin dichloride, di-t-butyltin dibromide, di-n-butyltin dichloride, di-n-butyltin dibromide, tri-n-butyltin chloride, tri-n-butyltin bromide, methylmagnesium iodide, dimethylaluminum iodide, diethylaluminum iodide, di-n-butylaluminum iodide, diisobutylaluminum iodide, di-n-octylaluminum iodide, methylaluminum diiodide, ethylaluminum diiodide, n-butylaluminum diiodide, isobutylaluminum diiodide, methylaluminum sesquiiodide, ethylaluminum sesquiiodide, isobutylaluminum sesquiiodide, ethylmagnesium iodide, n-butylmagnesium iodide, isobutylmagnesium iodide, phenylmagnesium iodide, benzylmagnesium iodide, trimethyltin iodide, triethyltin iodide, tri-n-butyltin iodide, di-n-butyltin diiodide, or di-t-butyl tin diiodide.

Also, the catalyst composition according to the embodiment of the present invention may include the halide in an amount of 1 mol to 20 mol, particularly 1 mol to 5 mol, and more particularly 2 mol to 3 mol based on 1 mol of the lanthanide rare earth element-containing compound. In a case in which the halide is included in an amount of greater than 20 mol, catalytic reaction control is not easy and an excessive amount of the halide may cause a side reaction.

Furthermore, the catalyst composition for preparing a conjugated diene polymer according to the embodiment of the present invention may include a non-coordinating anion-containing compound or a non-coordinating anion precursor compound instead of the halide or with the halide.

Specifically, in the compound containing a non-coordinating anion, the non-coordinating anion is a sterically bulky anion that does not form a coordinate bond with an active center of a catalyst system due to steric hindrance, wherein the non-coordinating anion may be a tetraarylborate anion or a fluorinated tetraarylborate anion. Also, the compound containing a non-coordinating anion may include a counter cation, for example, a carbonium cation such as a triarylcarbonium cation; an ammonium cation, such as N,N-dialkyl anilinium cation, or a phosphonium cation, in addition to the above-described non-coordinating anion. For example, the compound containing a non-coordinating anion may include triphenylcarbonium tetrakis(pentafluorophenyl)borate, N,N-dimethylanilinium tetrakis(pentafluorophenyl)borate, triphenylcarbonium tetrakis[3,5-bis(trifluoromethyl)phenyl]borate, or N,N-dimethylanilinium tetrakis [3,5-bis(trifluoromethyl)phenyl]borate.

Also, the non-coordinating anion precursor, as a compound capable of forming a non-coordinating anion under the reaction conditions, may include a triaryl boron compound ($BE_3$, where E is a strong electron-withdrawing aryl group such as a pentafluorophenyl group or 3,5-bis(trifluoromethyl)phenyl group).

(c) Conjugated Diene-Based Monomer

Also, the catalyst composition may further include a conjugated diene-based monomer, and, since the catalyst composition is used in the form of a performing catalyst composition in which a portion of the conjugated diene-based monomer used in the polymerization reaction is pre-polymerized by being premixed with the catalyst composition for polymerization, catalyst composition activity may not only be improved, but a conjugated diene-based polymer thus prepared may be stabilized.

In the present invention, the expression "preforming" may denote that, in a case in which a catalyst composition including a lanthanide rare earth element-containing compound, an alkylating agent, and a halide, that is, a catalyst system includes diisobutylaluminum hydride (DIBAH), a small amount of a conjugated diene-based monomer, such as 1,3-butadiene, is added to reduce the possibility of producing various catalytically active species, and pre-polymerization is performed in the catalyst composition system with the addition of the 1,3-butadiene. Also, the expression "premix" may denote a state in which each compound is uniformly mixed in the catalyst composition system without being polymerized.

In this case, with respect to the conjugated diene-based monomer used in the preparation of the catalyst composition, some amount within a total amount range of the conjugated diene-based monomer used in the polymerization reaction may be used, and, for example, the conjugated diene-based monomer may be used in an amount of 1 mol to 100 mol, for example, 10 mol to 50 mol, or 20 mol to 50 mol based on 1 mol of the lanthanide rare earth element-containing compound.

The catalyst composition according to the embodiment of the present invention may be prepared by sequentially mixing the above-described lanthanide rare earth element-containing compound and at least one of the alkylating agent, the halide, and the conjugated diene-based monomer, specifically, the lanthanide rare earth element-containing compound, alkylating agent, halide, and selectively conjugated diene-based monomer, in an organic solvent. In this case, the organic solvent may be a non-polar solvent that is not reactive with the above-described catalyst components. Specifically, the non-polar solvent may include linear, branched, or cyclic aliphatic hydrocarbon having 5 to 20 carbon atoms such as n-pentane, n-hexane, n-heptane, n-octane, n-nonane, n-decane, isopentane, isohexane, isoheptane, isooctane, 2,2-dimethylbutane, cyclopentane, cyclohexane, methylcyclopentane, or methylcyclohexane; a mixed solvent of aliphatic hydrocarbon having 5 to 20 carbon atoms such as petroleum ether or petroleum spirits, or kerosene; or an aromatic hydrocarbon-based solvent such as benzene, toluene, ethylbenzene, and xylene, and any one thereof or a mixture of two or more thereof may be used. The non-polar solvent may more specifically include the above-described linear, branched, or cyclic aliphatic hydrocarbon having 5 to 20 carbon atoms or the above-described mixed solvent of aliphatic hydrocarbon, and, for example, may include n-hexane, cyclohexane, or a mixture thereof.

Also, the organic solvent may be appropriately selected depending on a type of the constituent material constituting the catalyst composition, particularly, the alkylating agent.

Specifically, since alkylaluminoxane, such as methylaluminoxane (MAO) or ethylaluminoxane, as the alkylating agent, is not easily dissolved in an aliphatic hydrocarbon-based solvent, an aromatic hydrocarbon-based solvent may be appropriately used.

Furthermore, in a case in which modified methylaluminoxane is used as the alkylating agent, an aliphatic hydrocarbon-based solvent may be appropriately used. In this case, since a single solvent system may be realized with an aliphatic hydrocarbon-based solvent, such as hexane, mainly used as a polymerization solvent, it may be more advantageous to the polymerization reaction. Also, the aliphatic hydrocarbon-based solvent may promote catalytic activity, and may further improve reactivity by the catalytic activity.

The organic solvent may be used in an amount of 20 mol to 20,000 mol, for example, 100 mol to 1,000 mol, based on 1 mol of the lanthanide rare earth element-containing compound.

The polymerization of step 1 may be performed by coordination anionic polymerization or radical polymerization, may specifically be bulk polymerization, solution polymerization, suspension polymerization, or emulsion polymerization, and, for example, may be solution polymerization.

Also, the polymerization may be performed by any method of batch and continuous methods. Specifically, the polymerization of step 1 may be performed by adding the conjugated diene-based monomer to the catalyst composition and performing a reaction in the organic solvent.

Herein, the organic solvent may be further added in addition to the amount of the organic solvent which may be used in the preparation of the catalyst composition, and specific types thereof may be the same as described above. Also, when the organic solvent is used, a concentration of the monomer may be in a range of 3 wt % to 80 wt %, or 10 wt % to 30 wt %.

Also, during the polymerization, an additive, for example, a reaction terminating agent for the completion of the polymerization reaction, such as polyoxyethylene glycol phosphate; or an antioxidant, such as 2,6-di-t-butylparacresol, may be further used. In addition, an additive that usually facilitates solution polymerization, specifically, an additive, such as a chelating agent, a dispersant, a pH adjuster, a deoxidizer, or an oxygen scavenger, may be further selectively used.

Furthermore, the polymerization may be temperature rise polymerization, isothermal polymerization, or constant temperature polymerization (adiabatic polymerization).

Herein, the constant temperature polymerization denotes a polymerization method including a step of performing polymerization not by randomly applying heat but with its own reaction heat after the organometallic compound is added, the temperature rise polymerization denotes a polymerization method in which the temperature is increased by randomly applying heat after the organometallic compound is added, and the isothermal polymerization denotes a polymerization method in which the temperature of the polymer is constantly maintained by taking away heat or applying heat after the organometallic compound is added.

The polymerization may be performed in a temperature range of −20° C. to 200° C., particularly in a temperature range of 20° C. to 150° C., and more particularly in a temperature range of 10° C. to 120° C. for 15 minutes to 3 hours. In a case in which the temperature during the polymerization is greater than 200° C., it is difficult to sufficiently control the polymerization reaction and the cis-1,4 bond content of the formed diene-based polymer may be decreased, and, in a case in which the temperature is less than −20° C., polymerization rate and efficiency may be reduced.

Step 2 is a step of reacting the active polymer with the modifier represented by Formula 1, in order to prepare a conjugated diene-based polymer.

The modifier represented by Formula 1 may be the same as described above, and at least one type thereof may be mixed and used in the reaction.

The modifier represented by Formula 1 may be used in an amount of 0.5 mol to 20 mol based on 1 mol of the lanthanide rare earth element-containing compound in the catalyst composition. Specifically, the modifier represented by Formula 1 may be used in an amount of 1 mol to 10 mol based on 1 mol of the lanthanide rare earth element-containing compound in the catalyst composition. Since the optimal modification reaction may be performed when the modifier is used in an amount that satisfies the above range, a conjugated diene-based polymer having a high modification ratio may be obtained.

The reaction of step 2 is a modification reaction for the introduction of a functional group into the polymer, wherein the reaction may be performed in a temperature range of 0° C. to 90° C. for 1 minute to 5 hours.

Also, the method of preparing a modified conjugated diene-based polymer according to the embodiment of the present invention may be performed by a batch polymerization method or a continuous polymerization method including one or more reactors.

After the completion of the above-described modification reaction, the polymerization reaction may be stopped by adding an isopropanol solution of 2,6-di-t-butyl-p-cresol (BHT) to a polymerization reaction system. Thereafter, a modified conjugated diene-based polymer may be obtained through a desolvation treatment, such as steam stripping in which a partial pressure of the solvent is reduced by supplying water vapor, or a vacuum drying treatment. Also, in addition to the above-described modified conjugated diene-based polymer, an unmodified active polymer may be included in a reaction product obtained as a result of the above-described modification reaction.

The preparation method according to the embodiment of the present invention may further include at least one step of recovering solvent and unreacted monomer and drying, if necessary, after step 2.

Furthermore, the present invention provides a rubber composition including the above modified conjugated diene-based polymer and a molded article prepared from the rubber composition.

The rubber composition according to an embodiment of the present invention may include the modified conjugated diene-based polymer in an amount of 0.1 wt % or more to 100 wt % or less, particularly 10 wt % to 100 wt %, and more particularly 20 wt % to 90 wt %. In a case in which the amount of the modified conjugated diene-based polymer is less than 0.1 wt %, an effect of improving abrasion resistance and crack resistance of a molded article prepared by using the rubber composition, for example, a tire, may be insignificant.

Also, the rubber composition may further include other rubber components, if necessary, in addition to the modified conjugated diene-based polymer, and, in this case, the rubber component may be included in an amount of 90 wt % or less based on a total weight of the rubber composition. Specifically, the rubber component may be included in an amount of 1 part by weight to 900 parts by weight based on 100 parts by weight of the modified conjugated diene-based polymer.

The rubber component may be a natural rubber or a synthetic rubber, and, for example, the rubber component may be a natural rubber (NR) including cis-1,4-polyisoprene; a modified natural rubber, such as an epoxidized natural rubber (ENR), a deproteinized natural rubber (DPNR), and a hydrogenated natural rubber, in which the general natural rubber is modified or purified; and a synthetic rubber such as a styrene-butadiene rubber (SBR), polybutadiene (BR), polyisoprene (IR), a butyl rubber (IIR), an ethylene-propylene copolymer, polyisobutylene-co-isoprene, neoprene, poly(ethylene-co-propylene), poly(styrene-co-butadiene), poly(styrene-co-isoprene), poly(styrene-co-isoprene-co-butadiene), poly(isoprene-co-butadiene), poly(ethylene-co-propylene-co-diene), a polysulfide rubber, an acrylic rubber, an urethane rubber, a silicon rubber, an epichlorohydrin rubber, a butyl rubber, and a halogenated butyl rubber. Any one thereof or a mixture of two or more thereof may be used.

Furthermore, the rubber composition may include 0.1 part by weight to 150 parts by weight of a filler based on 100 parts by weight of the modified conjugated diene-based polymer, and the filler may include a silica-based filler, a carbon black-based filler, or a combination thereof. Specifically, the filler may be carbon black.

The carbon black-based filler is not particularly limited, but, for example, may have a nitrogen surface area per gram ($N_2SA$, measured according to JIS K 6217-2:2001) of 20 $m^2/g$ to 250 $m^2/g$. Also, the carbon black may have a dibutyl phthalate (DBP) oil absorption of 80 cc/100 g to 200 cc/100 g. If the nitrogen surface area per gram of the carbon black is greater than 250 $m^2/g$, processability of the rubber composition may be reduced, and, if the nitrogen surface area per gram of the carbon black is less than 20 $m^2/g$, reinforcement by carbon black may be insignificant. Furthermore, if the DBP oil absorption of the carbon black is greater than 200 cc/100 g, the processability of the rubber composition may be reduced, and, if the DBP oil absorption of the carbon black is less than 80 cc/100 g, the reinforcement by carbon black may be insignificant.

Also, the silica-based filler is not particularly limited, but, for example, may include wet silica (hydrous silicic acid), dry silica (anhydrous silicic acid), calcium silicate, aluminum silicate, or colloidal silica. Specifically, the silica-based filler may be wet silica in which an effect of improving both fracture characteristics and wet grip is the most significant. Furthermore, the silica may have a nitrogen surface area per gram ($N_2SA$) of 120 $m^2$/g to 180 $m^2$/g, and a cetyltrimethylammonium bromide (CTAB) surface area per gram of 100 $m^2$/g to 200 $m^2$/g. If the nitrogen surface area per gram of the silica is less than 120 $m^2$/g, reinforcement by silica may be insignificant, and, if the nitrogen surface area per gram of the silica is greater than 180 $m^2$/g, the processability of the rubber composition may be reduced. Also, if the CTAB surface area per gram of the silica is less than 100 $m^2$/g, the reinforcement by silica, as the filler, may be insignificant, and, if the CTAB surface area per gram of the silica is greater than 200 $m^2$/g, the processability of the rubber composition may be reduced.

In a case in which silica is used as the filler, a silane coupling agent may be used together for the improvement of reinforcement and low heat generation property.

Specific examples of the silane coupling agent may be bis(3-triethoxysilylpropyl)tetrasulfide, bis(3-triethoxysilylpropyl)trisulfide, bis(3-triethoxysilylpropyl)disulfide, bis(2-triethoxysilylethyl)tetrasulfide, bis(3-trimethoxysilylpropyl)tetrasulfide, bis(2-trimethoxysilylethyl)tetrasulfide, 3-mercaptopropyl trimethoxysilane, 3-mercaptopropyl triethoxysilane, 2-mercaptoethyl trimethoxysilane, 2-mercaptoethyl triethoxysilane, 3-trimethoxysilylpropyl-N,N-dimethylthiocarbamoyl tetrasulfide, 3-triethoxysilylpropyl-N,N-dimethylthiocarbamoyl tetrasulfide, 2-triethoxysilylethyl-N,N-dimethylthiocarbamoyl tetrasulfide, 3-trimethoxysilylpropyl benzothiazolyl tetrasulfide, 3-triethoxysilylpropyl benzolyl tetrasulfide, 3-triethoxysilylpropyl methacrylate monosulfide, 3-trimethoxysilylpropyl methacrylate monosulfide, bis(3-diethoxymethylsilylpropyl)tetrasulfide, 3-mercaptopropyl dimethoxymethylsilane, dimethoxymethylsilylpropyl-N,N-dimethylthiocarbamoyl tetrasulfide, or dimethoxymethylsilylpropyl benzothiazolyl tetrasulfide, and any one thereof or a mixture of two or more thereof may be used. For example, in consideration of the effect of improving the reinforcement, the silane coupling agent may be bis(3-triethoxysilylpropyl)polysulfide or 3-trimethoxysilylpropyl benzothiazyl tetrasulfide.

Furthermore, in the rubber composition according to the embodiment of the present invention, since the modified conjugated diene-based polymer, in which a function group having a high affinity with the silica is introduced into the active site, is used as the rubber component, a mixing amount of the silane coupling agent may be reduced in comparison to a conventional case. Specifically, the silane coupling agent may be used in an amount of 1 part by weight to 20 parts by weight based on 100 parts by weight of the silica. In a case in which the silane coupling agent is used within the above range, the silane coupling agent may prevent gelation of the rubber component while sufficiently having an effect as a coupling agent. For example, the silane coupling agent may be used in an amount of 5 parts by weight to 15 parts by weight based on 100 parts by weight of the silica.

Also, the rubber composition according to the embodiment of the present invention may be sulfur cross-linkable, and, accordingly, may further include a vulcanizing agent.

The vulcanizing agent may specifically be sulfur powder and may be included in an amount of 0.1 part by weight to 10 parts by weight based on 100 parts by weight of the rubber component. When the vulcanizing agent is included within the above range, elastic modulus and strength required for the vulcanized rubber composition may be secured and, simultaneously, a low fuel consumption property may be obtained.

Furthermore, the rubber composition according to the embodiment of the present invention may further include various additives, such as a vulcanization accelerator, process oil, a plasticizer, an antioxidant, a scorch inhibitor, zinc white, stearic acid, a thermosetting resin, or a thermoplastic resin, used in the general rubber industry, in addition to the above-described components.

The vulcanization accelerator is not particularly limited, but, specifically, a thiazole-based compound, such as 2-mercaptobenzothiazole (M), dibenzothiazyl disulfide (DM), and N-cyclohexylbenzothiazole-2-sulfenamide (CZ), or a guanidine-based compound, such as diphenylguanidine (DPG), may be used. The vulcanization accelerator may be included in an amount of 0.1 part by weight to 5 parts by weight based on 100 parts by weight of the rubber component.

Also, the process oil acts as a softener in the rubber composition, wherein the process oil may be a paraffin-based, naphthenic-based, or aromatic-based compound, and, for example, the aromatic-based compound may be used in consideration of tensile strength and abrasion resistance, and the naphthenic-based or paraffin-based process oil may be used in consideration of hysteresis loss and low temperature characteristics. The process oil may be included in an amount of 100 parts by weight or less based on 100 parts by weight of the rubber component, and, when the process oil is included in the above amount, decreases in tensile strength and low heat generation property (low fuel consumption property) of the vulcanized rubber may be prevented.

Furthermore, specific examples of the antioxidant may be N-isopropyl-N'-phenyl-p-phenylenediamine, N-(1,3-dimethylbutyl)-N'-phenyl-p-phenylenediamine, 6-ethoxy-2,2,4-trimethyl-1,2-dihydroquinoline, or a high-temperature condensate of diphenylamine and acetone. The antioxidant may be used in an amount of 0.1 part by weight to 6 parts by weight based on 100 parts by weight of the rubber component.

The rubber composition according to the embodiment of the present invention may be obtained by kneading the above mixing formulation using a kneader such as a Banbury mixer, a roll, and an internal mixer, and a rubber composition having excellent abrasion resistance as well as low heat generation property may also be obtained by a vulcanization process after molding.

Accordingly, the rubber composition may be suitable for the preparation of each member of a tire, such as a tire's tread, an under tread, a sidewall, a carcass coating rubber, a belt coating rubber, a bead filler, a chafer, or a bead coating rubber, or various industrial rubber products such as an anti-vibration rubber, a belt conveyor, and a hose.

The molded article prepared by using the rubber composition may include a tire or a tire's tread.

Hereinafter, the present invention will be described in more detail, according to specific examples and experimental examples. However, the following examples and experimental examples are merely presented to exemplify the present invention, and the scope of the present invention is not limited thereto.

Preparation Example 1: Preparation of Modifier Represented by Formula 1-1

1) Preparation of Ethyl 6-Aminohexanoate Hydrochloride

After 240.0 g (1.83 mol) of 6-aminohexanoic acid was put in a 2 L round-bottom flask and 80 ml of ethanol was added thereto, the temperature was set at 0° C. Thereafter, a reaction was performed while 126.77 ml (1.74 mol) of thionyl chloride was slowly added for 30 minutes. When the exothermic process ended, a reaction was performed at room temperature for 12 hours or more, the reaction was then terminated, and the solvent was removed under reduced pressure. After 1 L of n-hexane was put and stirred for 30 minutes, the solution was filtered. After 1 L of diethyl ether was put, secondary stirring was performed, and the solution thus obtained was filtered and then concentrated to obtain 347.4 g (yield: 97%) of ethyl 6-aminohexanoate hydrochloride. $^1$H nuclear magnetic resonance spectroscopic data of the ethyl 6-aminohexanoate hydrochloride are as follows.

$^1$H-NMR (500 MHz, CDCl$_3$) δ 8.30 (s, 3H), 4.14-4.10 (q, 2H), 3.03-3.00 (t, 2H), 2.33-2.30 (t, 2H), 1.82-1.79 (t, 2H), 1.68-1.65 (t, 2H), 1.47-1.44 (t, 2H), 1.26-1.23 (t, 3H).

2) Preparation of Ethyl 6-Aminohexanoate

After 340.0 g (1.74 mol) of the ethyl 6-aminohexanoate hydrochloride prepared in 1) was put in a 2 L round-bottom flask and 700 ml of dichloromethane was added thereto, the temperature was set at 0° C. Thereafter, a reaction was performed for 12 hours by slowly increasing the temperature to room temperature while 605.86 ml (4.34 mol) of triethylamine was slowly added for 30 minutes, and the reaction was then terminated. After 500 ml of water was added to extract an organic layer, sodium sulfate was added to the organic layer, filtered, and then concentrated to obtain 273.7 g (yield: 98.9%) of ethyl 6-aminohexanoate. 1H nuclear magnetic resonance spectroscopic data of the ethyl 6-aminohexanoate are as follows.

$^1$H-NMR (500 MHz, CDCl$_3$) δ 4.13-4.09 (q, 2H), 2.69-2.67 (t, 2H), 2.30-2.27 (t, 2H), 1.60 (m, 2H), 1.48-1.42 (m, 2H), 1.37-1.31 (m, 2H), 1.25-1.23 (t, 2H), 1.19 (s, 3H).

3) Preparation of Modifier Represented by Formula 1-1

After 170.0 g (1.07 mol) of the ethyl 6-aminohexanoate prepared in 2) was put in a 1 L round-bottom flask and 267 ml (2.14 mol) of methyl isobutyl ketone was added thereto, a reaction was performed for 12 hours by increasing the temperature to 135° C. using a Dean-Stark apparatus, and the reaction was then terminated. The remaining methyl isobutyl ketone was removed to prepare 240.3 g (yield: 93.2%) of a compound represented by Formula 1-1 below. $^1$H nuclear magnetic resonance spectroscopic data of Formula 1-1 are as follows.

[Formula 1-1]

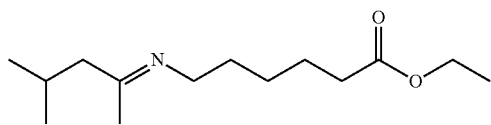

$^1$H-NMR (500 MHz, CDCl$_3$) δ 4.13-4.09 (q, 2H), 3.23-3.20 (t, 2H), 2.31-2.29 (t, 2H), 2.12-2.10 (m, 2H), 1.77 (s, 3H), 1.69-1.61 (m, 4H), 1.40-1.34 (m, 2H), 1.26-1.23 (t, 2H), 0.92-0.88 (m, 6H).

Preparation Example 2: Preparation of Modifier Represented by Formula 1-2

1) Preparation of Ethyl 11-Aminoundecanoate Hydrochloride

After 30.0 g (149.02 mmol) of 11-aminoundecanoic acid was put in a 250 mL round-bottom flask and 100 ml of ethanol was added thereto, the temperature was set at 0° C. Thereafter, a reaction was performed while 10.33 ml (141.57 mmol) of thionyl chloride was slowly added for 30 minutes. When the exothermic process ended, a reaction was performed at room temperature for 12 hours or more, the reaction was then terminated, and the solvent was removed under reduced pressure. After 500 mL of n-hexane was put and stirred for 30 minutes, the solution was filtered. After 500 mL of diethyl ether was put, secondary stirring was performed, and the solution thus obtained was filtered and then concentrated to obtain 38.4 g (yield: 97%) of ethyl 11-aminoundecanoate hydrochloride. $^1$H nuclear magnetic resonance spectroscopic data of the ethyl 11-aminoundecanoate hydrochloride are as follows.

$^1$H-NMR (500 MHz, CDCl$_3$) δ 8.32 (s, 3H), 4.14-4.10 (q, 2H), 3.99-2.96 (t, 2H), 2.30-2.27 (t, 2H), 1.79-1.73 (m, 2H), 1.62-1.58 (m, 2H), 1.39-1.37 (m, 2H), 1.28-1.24 (t, 13H).

2) Preparation of Ethyl 11-Aminoundecanoate

After 36.6 g (137.69 mmol) of the ethyl 11-aminoundecanoate hydrochloride prepared in 1) was put in a 250 mL round-bottom flask and 100 ml of dichloromethane was added thereto, the temperature was set at 0° C. Thereafter, a reaction was performed for 12 hours by slowly increasing the temperature to room temperature while 28.81 ml (206.53 mmol) of triethylamine was slowly added for 30 minutes, and the reaction was then terminated. After 500 ml of water was added to extract an organic layer, sodium sulfate was added to the organic layer, filtered, and then concentrated to obtain 37.8 g (yield: 97.8%) of ethyl 11-aminoundecanoate. $^1$H nuclear magnetic resonance spectroscopic data of the ethyl 11-aminoundecanoate are as follows.

$^1$H-NMR (500 MHz, CDCl$_3$) δ 4.13-4.09 (q, 2H), 2.68-2.66 (t, 2H), 2.28 (t, 2H), 1.61-1.58 (m, 2H), 1.54-1.51 (m, 2H), 1.44-1.40 (m, 2H), 1.27-1.22 (m, 15H).

3) Preparation of Modifier Represented by Formula 1-2

After 30.0 g (130.80 mmol) of the ethyl 11-aminoundecanoate prepared in 2) was put in a 500 mL round-bottom flask and 32.71 ml (261.92 mmol) of methyl isobutyl ketone was added thereto, a reaction was performed for 12 hours by increasing the temperature to 135° C. using a Dean-Stark apparatus, and the reaction was then terminated. The remaining methyl isobutyl ketone was removed to prepare 38.1 g (yield: 93.5%) of a compound represented by Formula 1-2 below. $^1$H nuclear magnetic resonance spectroscopic data of Formula 1-2 are as follows.

[Formula 1-2]

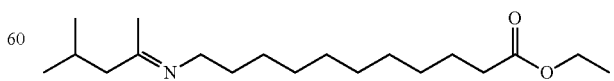

$^1$H-NMR (500 MHz, CDCl$_3$) δ 4.14-4.10 (q, 2H), 3.26-3.21 (m, 2H), 2.29-2.26 (t, 2H), 2.12-2.10 (m, 2H), 1.97-1.92 (m, 2H), 1.77 (s, 3H), 1.63-1.56 (m, 4H), 1.27-1.23 (m, 11H), 1.26-1.23 (t, 3H), 0.93-0.87 (m, 6H).

Preparation Example 3: Preparation of Modifier Represented by Formula 1-3

1) Preparation of Ethyl 4-Aminobutanoate Hydrochloride

After 200.0 g (1.94 mol) of 4-aminobutanoic acid was put in a 2 L round-bottom flask and 500 ml of ethanol was added thereto, the temperature was set at 0° C. Thereafter, a reaction was performed while 134.38 ml (1.84 mol) of thionyl chloride was slowly added for 30 minutes. When the exothermic process ended, a reaction was performed at room temperature for 12 hours or more, the reaction was then terminated, and the solvent was removed under reduced pressure. After 1 L of n-hexane was put and stirred for 30 minutes, the solution was filtered. After 1 L of diethyl ether was put, secondary stirring was performed, and the solution thus obtained was filtered and then concentrated to obtain 315.7 g (yield: 97%) of ethyl 4-aminobutanoate hydrochloride. $^1$H nuclear magnetic resonance spectroscopic data of the ethyl 4-aminobutanoate hydrochloride are as follows.

$^1$H-NMR (500 MHz, CDCl$_3$) δ 8.27 (br, s, 3H), 4.16-4.12 (q, 2H), 3.15-3.10 (m, 2H), 2.52-2.50 (t, 2H), 2.12-2.10 (t, 2H), 1.24-1.25 (t, 3H).

2) Preparation of Ethyl 4-Aminobutanoate

After 300.0 g (1.79 mol) of the ethyl 4-aminobutanoate hydrochloride prepared in 1) was put in a 2 L round-bottom flask and 600 ml of dichloromethane was added thereto, the temperature was set at 0° C. Thereafter, a reaction was performed for 12 hours by slowly increasing the temperature to room temperature while 374.43 ml (2.68 mol) of triethylamine was slowly added for 30 minutes, and the reaction was then terminated. After 500 ml of water was added to extract an organic layer, sodium sulfate was added to the organic layer, filtered, and then concentrated to obtain 230.6 g (yield: 98.2%) of ethyl 4-aminobutanoate. 1H nuclear magnetic resonance spectroscopic data of the ethyl 4-aminobutanoate are as follows.

$^1$H-NMR (500 MHz, CDCl$_3$) δ 4.13-4.09 (q, 2H), 2.68-2.66 (t, 2H), 2.46-2.44 (t, 2H), 2.06-2.02 (m, 2H), 1.25-1.22 (t, 3H), 1.18 (s, 2H).

3) Preparation of Modifier Represented by Formula 1-3

After 220.0 g (1.68 mol) of the ethyl 4-aminobutanoate prepared in 2) was put in a 1 L round-bottom flask and 419.44 ml (3.35 mol) of methyl isobutyl ketone was added thereto, a reaction was performed for 12 hours by increasing the temperature to 135° C. using a Dean-Stark apparatus, and the reaction was then terminated. The remaining methyl isobutyl ketone was removed to prepare 335.7 g (yield: 93.8%) of a compound represented by Formula 1-3 below. $^1$H nuclear magnetic resonance spectroscopic data of Formula 1-3 are as follows.

[Formula 1-3]

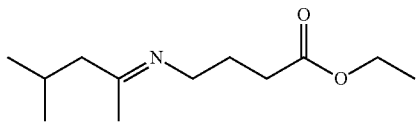

$^1$H-NMR (500 MHz, CDCl$_3$) δ 4.12-4.08 (q, 2H), 3.21-3.18 (t, 2H), 2.30-2.28 (t, 2H), 2.10-2.08 (m, 2H), 1.76 (s, 3H), 1.69-1.61 (m, 3H), 1.25-1.22 (t, 3H), 0.92-0.88 (d, 6H).

Preparation Example 4: Preparation of Modifier Represented by Formula 1-4

1) Preparation of Butyl 6-Aminohexanoate Hydrochloride

After 204.0 g (1.52 mol) of 6-aminohexanoic acid was put in a 2 L round-bottom flask and 600 ml of n-butanol was added thereto, the temperature was set at 0° C. Thereafter, a reaction was performed while 100.15 ml (1.37 mol) of thionyl chloride was slowly added for 30 minutes. When the exothermic process ended, a reaction was performed at room temperature for 12 hours or more, the reaction was then terminated, and the solvent was removed under reduced pressure. After 1 L of n-hexane was put and stirred for 30 minutes, the solution was filtered. After 1 L of diethyl ether was put, secondary stirring was performed, and the solution thus obtained was filtered and then concentrated to obtain 328.9 g (yield: 96.4%) of butyl 6-aminohexanoate hydrochloride. $^1$H nuclear magnetic resonance spectroscopic data of the butyl 6-aminohexanoate hydrochloride are as follows.

$^1$H-NMR (500 MHz, CDCl$_3$) δ 8.28 (s, 3H), 4.13-4.09 (q, 2H), 3.02-2.99 (t, 2H), 2.33-2.30 (t, 2H), 1.81-1.78 (t, 2H), 1.67-1.64 (t, 2H), 1.47-1.44 (t, 2H), 1.34-1.31 (m, 2H), 1.25-1.22 (m, 2H), 0.94-0.91 (t, 3H).

2) Preparation of Butyl 6-Aminohexanoate

After 300.0 g (1.34 mol) of the butyl 6-aminohexanoate hydrochloride prepared in 1) was put in a 2 L round-bottom flask and 600 ml of dichloromethane was added thereto, the temperature was set at 0° C. Thereafter, a reaction was performed for 12 hours by slowly increasing the temperature to room temperature while 280.34 ml (2.01 mol) of triethylamine was slowly added for 30 minutes, and the reaction was then terminated. After 400 ml of water was added to extract an organic layer, sodium sulfate was added to the organic layer, filtered, and then concentrated to obtain 244.5 g (yield: 97.4%) of butyl 6-aminohexanoate. 1H nuclear magnetic resonance spectroscopic data of the butyl 6-aminohexanoate are as follows.

$^1$H-NMR (500 MHz, CDCl$_3$) δ 4.14-4.10 (q, 2H), 3.03-3.00 (t, 2H), 2.34-2.31 (t, 2H), 1.80-1.77 (t, 2H), 1.65-1.62 (t, 2H), 1.46-1.43 (t, 2H), 1.31-1.28 (m, 2H), 1.24-1.21 (m, 2H), 1.19 (s, 2H), 0.92-0.89 (t, 3H).

3) Preparation of Modifier Represented by Formula 1-4

After 220.0 g (1.17 mol) of the butyl 6-aminohexanoate prepared in 2) was put in a 1 L round-bottom flask and 293.8 ml (2.35 mol) of methyl isobutyl ketone was added thereto, a reaction was performed for 12 hours by increasing the temperature to 135° C. using a Dean-Stark apparatus, and the reaction was then terminated. The remaining methyl isobutyl ketone was removed to prepare 294.1 g (yield: 92.9%) of a compound represented by Formula 1-4 below. $^1$H nuclear magnetic resonance spectroscopic data of Formula 1-4 are as follows.

[Formula 1-4]

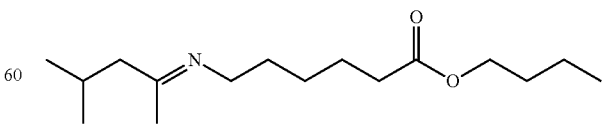

$^1$H-NMR (500 MHz, CDCl$_3$) δ 4.14-4.10 (q, 2H), 3.24-3.21 (t, 2H), 2.32-2.29 (t, 2H), 2.12-2.10 (m, 2H), 1.98-1.92 (m, 2H), 1.77 (s, 3H), 1.70-1.65 (m, 3H), 1.40-1.34 (m, 2H), 1.26-1.23 (t, 2H), 1.24-1.21 (m, 2H), 0.92-0.84 (m, 9H).

Example 1

900 g of 1,3-butadiene and 6.6 kg of n-hexane were added to a 20 L autoclave reactor, and an internal temperature of the reactor was then increased to 70° C. After a catalyst composition, which was prepared by a reaction of a hexane solution, in which 0.10 mmol of $Nd(2,2$-diethyl decanoate$)_3$ was dissolved, with 0.89 mmol of diisobutylaluminum hydride (DIBAH), 0.24 mmol of diethylaluminum chloride, and 3.3 mmol of 1,3-butadiene, was added to the reactor, polymerization was performed for 60 minutes. Thereafter, a hexane solution including 0.23 mmol of the modifier represented by Formula 1-1, which was prepared in Preparation Example 1, was added, and a modification reaction was then performed at 70° C. for 30 minutes. Thereafter, a hexane solution, in which 1.0 g of a polymerization terminator was included, and 33 g of a solution, in which 30 wt % of WINGSTAY (Eliokem SAS, France), as an antioxidant, was dissolved in hexane, were added. A polymer thus obtained was put in hot water heated by steam and stirred to remove the solvent, and was then roll-dried to remove the remaining solvent and water to prepare a modified butadiene polymer.

Example 2

900 g of 1,3-butadiene and 6.6 kg of n-hexane were added to a 20 L autoclave reactor, and an internal temperature of the reactor was then increased to 70° C. After a catalyst composition, which was prepared by a reaction of a hexane solution, in which 0.10 mmol of $Nd(2,2$-diethyl decanoate$)_3$ was dissolved, with 0.89 mmol of diisobutylaluminum hydride (DIBAH), 0.24 mmol of diethylaluminum chloride, and 3.3 mmol of 1,3-butadiene, was added to the reactor, polymerization was performed for 60 minutes. Thereafter, a hexane solution including 0.23 mmol of the modifier represented by Formula 1-2, which was prepared in Preparation Example 2, was added, and a modification reaction was then performed at 70° C. for 30 minutes. Thereafter, a hexane solution, in which 1.0 g of a polymerization terminator was included, and 33 g of a solution, in which 30 wt % of WINGSTAY (Eliokem SAS, France), as an antioxidant, was dissolved in hexane, were added. A polymer thus obtained was put in hot water heated by steam and stirred to remove the solvent, and was then roll-dried to remove the remaining solvent and water to prepare a modified butadiene polymer.

Example 3

900 g of 1,3-butadiene and 6.6 kg of n-hexane were added to a 20 L autoclave reactor, and an internal temperature of the reactor was then increased to 70° C. After a catalyst composition, which was prepared by a reaction of a hexane solution, in which 0.10 mmol of $Nd(2,2$-diethyl decanoate$)_3$ was dissolved, with 0.89 mmol of diisobutylaluminum hydride (DIBAH), 0.24 mmol of diethylaluminum chloride, and 3.3 mmol of 1,3-butadiene, was added to the reactor, polymerization was performed for 60 minutes. Thereafter, a hexane solution including 0.23 mmol of the modifier represented by Formula 1-3, which was prepared in Preparation Example 3, was added, and a modification reaction was then performed at 70° C. for 30 minutes. Thereafter, a hexane solution, in which 1.0 g of a polymerization terminator was included, and 33 g of a solution, in which 30 wt % of WINGSTAY (Eliokem SAS, France), as an antioxidant, was dissolved in hexane, were added. A polymer thus obtained was put in hot water heated by steam and stirred to remove the solvent, and was then roll-dried to remove the remaining solvent and water to prepare a modified butadiene polymer.

Example 4

900 g of 1,3-butadiene and 6.6 kg of n-hexane were added to a 20 L autoclave reactor, and an internal temperature of the reactor was then increased to 70° C. After a catalyst composition, which was prepared by a reaction of a hexane solution, in which 0.10 mmol of $Nd(2,2$-diethyl decanoate$)_3$ was dissolved, with 0.89 mmol of diisobutylaluminum hydride (DIBAH), 0.24 mmol of diethylaluminum chloride, and 3.3 mmol of 1,3-butadiene, was added to the reactor, polymerization was performed for 60 minutes. Thereafter, a hexane solution including 0.23 mmol of the modifier represented by Formula 1-4, which was prepared in Preparation Example 4, was added, and a modification reaction was then performed at 70° C. for 30 minutes. Thereafter, a hexane solution, in which 1.0 g of a polymerization terminator was included, and 33 g of a solution, in which 30 wt % of WINGSTAY (Eliokem SAS, France), as an antioxidant, was dissolved in hexane, were added. A polymer thus obtained was put in hot water heated by steam and stirred to remove the solvent, and was then roll-dried to remove the remaining solvent and water to prepare a modified butadiene polymer.

Comparative Example 900 g of 1,3-butadiene and 6.6 kg of n-hexane were added to a 20 L autoclave reactor, and an internal temperature of the reactor was then increased to 70° C. After a catalyst composition, which was prepared by a reaction of a hexane solution, in which 0.10 mmol of $Nd(2,2$-diethyl decanoate$)_3$ was dissolved, with 0.89 mmol of diisobutylaluminum hydride (DIBAH), 0.24 mmol of diethylaluminum chloride, and 3.3 mmol of 1,3-butadiene, was added to the reactor, polymerization was performed for 60 minutes. Thereafter, a hexane solution, in which 1.0 g of a polymerization terminator was included, and 33 g of a solution, in which 30 wt % of WINGSTAY (Eliokem SAS, France), as an antioxidant, was dissolved in hexane, were added. A polymer thus obtained was put in hot water heated by steam and stirred to remove the solvent, and was then roll-dried to remove the remaining solvent and water to prepare a butadiene polymer.

Experimental Example 1

Physical properties of each of the modified butadiene polymers prepared in Examples 1 to 4 and the butadiene polymer prepared in Comparative Example were respectively measured by the following methods, and the results thereof are presented in Table 1 below.

1) Weight-Average Molecular Weight (Mw), Number-Average Molecular Weight (Mn), and Molecular Weight Distribution Each polymer was dissolved in tetrahydrofuran (THF) at 40° C. for 30 minutes, and then loaded and flowed into a gel permeation chromatography (GPC) column. In this case, as the column, two PLgel Olexis (product name) columns by Polymer Laboratories and one PLgel mixed-C (product name) column by Polymer Laboratories were combined and used. Also, all newly replaced columns were mixed-bed type columns, and polystyrene was used as a GPC standard material.

2) Mooney Viscosity and –S/R Value

Mooney viscosity (MV) of each polymer was measured with a large rotor at a rotor speed of 2±0.02 rpm at 100° C.

using MV2000E by Monsanto Company. After each polymer was left standing for 30 minutes or more at room temperature (23±3° C.), 27±3 g of each polymer was taken as a sample used in this case and filled into a die cavity, and Mooney viscosity was measured while applying a torque by operating a platen.

Also, a change in the Mooney viscosity obtained while the torque was released during the measurement of the Mooney viscosity was observed for 1 minute, and a −S/R value was determined from its slope.

3) Cis-1,4 Bond Content

Fourier transform infrared spectroscopy was performed on each polymer, and a cis-1,4 bond content in the 1,4-cis polybutadiene was calculated from the result thereof.

of stearic acid were mixed with 100 parts by weight of each of the modified butadiene polymers and butadiene polymer to prepare each rubber composition. Thereafter, 2 parts by weight of sulfur, 2 parts by weight of a vulcanization accelerator (CZ), and 0.5 part by weight of a vulcanization accelerator (DPG) were added to each rubber composition, and vulcanization was performed at 160° C. for 25 minutes to prepare each rubber sample.

1) Mooney Viscosity (ML1+4)

Mooney viscosity of each rubber sample was measured with a large rotor at a rotor speed of 2±0.02 rpm at 100° C. using MV2000E by Monsanto Company.

TABLE 1

| Category | | Example 1 | Example 2 | Example 3 | Example 4 | Comparative Example |
|---|---|---|---|---|---|---|
| Whether or not modified | | Modified | Modified | Modified | Modified | Unmodified |
| GPC results | Mn (×10$^5$ g/mol) | 28.4 | 27.9 | 28.1 | 28.0 | 28.3 |
| | Mw (×10$^5$ g/mol) | 93.4 | 86.8 | 88.4 | 91.2 | 80.0 |
| | Mw/Mn | 3.29 | 3.11 | 3.14 | 3.25 | 2.83 |
| MV (ML1 + 4, @100° C.) (MU) | | 50.1 | 50.6 | 48.4 | 49.7 | 45.0 |
| −S/R | | 0.764 | 0.751 | 0.755 | 0.747 | 0.694 |
| Cis-1,4 bond content (%) | | 96.3 | 96.8 | 96.5 | 96.6 | 96.1 |

As illustrated in Table 1, it was confirmed that the modified butadiene polymers of Examples 1 to 4 according to the embodiment of the present invention had a −S/R value of 0.7 or more which was significantly increased in comparison to the butadiene polymer of Comparative Example. From this result, it may be confirmed that the modified butadiene polymers according to the embodiment of the present invention had high linearity.

Experimental Example 2

After rubber compositions and rubber samples were prepared by using the modified butadiene polymers prepared in Examples 1 to 4 and the butadiene polymer prepared in Comparative Example, Mooney viscosity, 300% modulus, and viscoelasticity were respectively measured by the following methods. Among them, index values in the 300% modulus and viscoelasticity were expressed by indexing measurement values of Comparative Example at 100. The results thereof are presented in Table 2 below.

Specifically, with respect to the rubber compositions, 70 parts by weight of carbon black, 22.5 parts by weight of process oil, 2 parts by weight of antioxidant (TMDQ), 3 parts by weight of zinc oxide (ZnO), and 2 parts by weight 2) Tensile Strength (Kg·f/Cm$^2$), 300% Modulus (Kg·f/Cm$^2$), and Elongation After the vulcanization of each rubber composition at 150° C. for 90 minutes, tensile strength of each vulcanizate, a modulus at 300% elongation (M-300%), and an elongation of each vulcanizate at break were measured according to ASTM D412.

3) Viscoelasticity (Tan δ @60° C.)

With respect to Tan δ property that is most important for low fuel consumption property, a viscoelastic coefficient (Tan δ) was measured at a frequency of 10 Hz, a prestrain of 5%, a dynamic strain of 3%, and a temperature of 60° C. using DMTS 500N by Gabo Instruments, Germany.

TABLE 2

| Category | Example 1 | Example 2 | Example 3 | Example 4 | Comparative Example |
|---|---|---|---|---|---|
| ML1 + 4 (FMB: Final Master batch) | 92.1 | 93.6 | 88.4 | 90.3 | 67 |
| M-300% (Index) | 110 (108) | 112 (110) | 106 (105) | 108 (107) | 101 (100) |
| tan δ @60° C. (Index) | 0.134 (106) | 0.132 (108) | 0.137 (104) | 0.135 (105) | 0.142 (100) |

As illustrated in Table 2, it was confirmed that Mooney viscosity characteristics, 300% moduli, and viscoelastic properties of the rubber samples, which were prepared by using the modified butadiene polymers of Examples 1 to 4 prepared by using the modifiers according to the embodiment of the present invention, were better than those of the rubber sample prepared by using the butadiene polymer of Comparative Example.

Specifically, with respect to the rubber samples which were prepared by using the modified butadiene polymers of Examples 1 to 4 prepared by using the modifiers according to the embodiment of the present invention, it was confirmed that tan δ values at 60° C. were reduced (indices were improved) while 300% moduli were significantly increased in comparison to that of the rubber sample prepared by using the unmodified butadiene polymer of Comparative Example. The results indicated that the modified butadiene polymer prepared by using the modifier according to the embodiment of the present invention may have high fuel efficiency as well as excellent rolling resistance (RR) characteristics while having excellent tensile properties.

The invention claimed is:

1. A modified conjugated diene-based polymer comprising a functional group derived from a modifier represented by Formula 1:

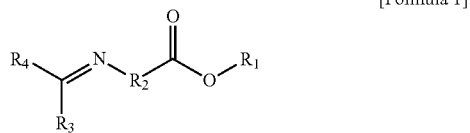

[Formula 1]

wherein, in Formula 1, $R_1$ is a monovalent hydrocarbon group having 1 to 20 carbon atoms; or a monovalent hydrocarbon group having 1 to 20 carbon atoms which includes at least one heteroatom selected from the group consisting of nitrogen (N), sulfur (S), and oxygen (O), $R_2$ is a divalent hydrocarbon group having 1 to 20 carbon atoms which is substituted or unsubstituted with at least one substituent selected from the group consisting of an alkyl group having 1 to 20 carbon atoms, a cycloalkyl group having 3 to 20 carbon atoms, and an aryl group having 6 to 30 carbon atoms; or a divalent hydrocarbon group having 1 to 20 carbon atoms which includes at least one heteroatom selected from the group consisting of N, S, and O, and $R_3$ and $R_4$ are each independently a monovalent hydrocarbon group having 1 to 20 carbon atoms which is substituted or unsubstituted with at least one substituent selected from the group consisting of an alkyl group having 1 to 20 carbon atoms, a cycloalkyl group having 3 to 20 carbon atoms, and an aryl group having 6 to 30 carbon atoms, or $R_3$ and $R_4$ are connected to each other to form an aliphatic or aromatic ring having 5 to 20 carbon atoms.

2. The modified conjugated diene-based polymer of claim 1, wherein the modifier represented by Formula 1 comprises compounds represented by Formulae 1-1 to 1-4:

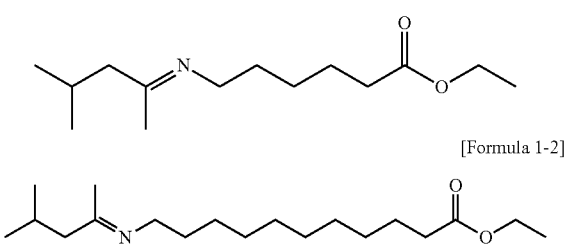

[Formula 1-1]

[Formula 1-2]

[Formula 1-3]

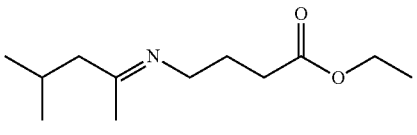

[Formula 1-4]

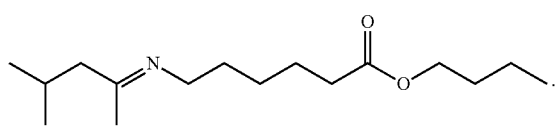

3. The modified conjugated diene-based polymer of claim 1, wherein the polymer has a number-average molecular weight of 100,000 g/mol to 700,000 g/mol.

4. The modified conjugated diene-based polymer of claim 1, wherein the polymer has a molecular weight distribution (Mw/Mn) of 1.05 to 5.

5. The modified conjugated diene-based polymer of claim 1, wherein the polymer has a −S/R (stress/relaxation) value at 100° C. of 0.7 or more.

6. A method of preparing the modified conjugated diene-based polymer of claim 1, the method comprising:

(1) preparing an active polymer coupled with an organometal by polymerization of a conjugated diene-based monomer in a hydrocarbon solvent in the presence of a catalyst composition including a lanthanide rare earth element-containing compound; and (2) reacting the active polymer with a modifier represented by Formula 1:

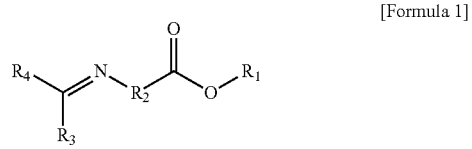

[Formula 1]

wherein, in Formula 1, $R_1$ is a monovalent hydrocarbon group having 1 to 20 carbon atoms; or a monovalent hydrocarbon group having 1 to 20 carbon atoms which includes at least one heteroatom selected from the group consisting of nitrogen (N), sulfur (S), and oxygen (O), $R_2$ is a divalent hydrocarbon group having 1 to 20 carbon atoms which is substituted or unsubstituted with at least one substituent selected from the group consisting of an alkyl group having 1 to 20 carbon atoms, a cycloalkyl group having 3 to 20 carbon atoms, and an aryl group having 6 to 30 carbon atoms; or a divalent hydrocarbon group having 1 to 20 carbon atoms which includes at least one heteroatom selected from the group consisting of N, S, and O, and $R_3$ and $R_4$ are each independently a monovalent hydrocarbon group having 1 to 20 carbon atoms which is substituted or unsubstituted with at least one substituent selected from the group consisting of an alkyl group having 1 to 20 carbon atoms, a cycloalkyl group having 3 to 20 carbon atoms, and an aryl group having 6 to 30 carbon atoms, or $R_3$ and $R_4$ are connected to each other to form an aliphatic or aromatic ring having 5 to 20 carbon atoms.

7. The method of claim 6, wherein the catalyst composition is used in an amount such that the lanthanide rare earth element-containing compound is included in an amount of 0.1 mmol to 0.5 mmol based on 100 g of the conjugated diene-based monomer.

8. The method of claim 6, wherein the lanthanide rare earth element-containing compound comprises a neodymium-based compound represented by Formula 5:

[Formula 5]

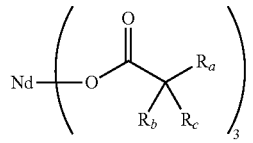

wherein, in Formula 5, $R_a$ to $R_c$ are each independently hydrogen or an alkyl group having 1 to 12 carbon atoms, but all of $R_a$ to $R_c$ are not hydrogen at the same time.

9. The method of claim 6, wherein the modifier is used in an amount of 0.5 mol to 20 mol based on 1 mol of the lanthanide rare earth element-containing compound.

* * * * *